United States Patent
Nappa et al.

(10) Patent No.: US 7,959,828 B2
(45) Date of Patent: *Jun. 14, 2011

(54) SOLVENT COMPOSITIONS COMPRISING UNSATURATED FLUORINATED HYDROCARBONS

(75) Inventors: Mario Joseph Nappa, Newark, DE (US); Melodie A. Schweitzer, Wilmington, DE (US); Allen Capron Sievert, Elkton, MD (US); Ekaterina N Swearingen, Wilmington, DE (US)

(73) Assignee: E. I. Du Pont de Nemours and Company, Wilmington, DE (US)

(*) Notice: Subject to any disclaimer, the term of this patent is extended or adjusted under 35 U.S.C. 154(b) by 88 days.

This patent is subject to a terminal disclaimer.

(21) Appl. No.: 12/714,709

(22) Filed: Mar. 1, 2010

(65) Prior Publication Data

US 2010/0152093 A1    Jun. 17, 2010

Related U.S. Application Data

(62) Division of application No. 11/591,650, filed on Nov. 1, 2006, now Pat. No. 7,700,004.

(60) Provisional application No. 60/732,771, filed on Nov. 1, 2005.

(51) Int. Cl.
    *B01F 1/00*    (2006.01)
    *C11D 7/30*    (2006.01)
    *B08B 3/08*    (2006.01)

(52) U.S. Cl. .............. 252/364; 252/67; 252/68; 252/69; 510/177; 510/178; 134/38; 134/42; 134/1.3; 134/34; 134/40; 427/58; 508/588

(58) Field of Classification Search .................. 252/364, 252/67, 68, 69; 510/177, 178; 134/38, 42, 134/1.3, 34, 40; 427/58; 508/588
See application file for complete search history.

(56) References Cited

U.S. PATENT DOCUMENTS

| | | | |
|---|---|---|---|
| 3,085,918 A | | 4/1963 | Sherliker et al. |
| 5,118,360 A | * | 6/1992 | Li et al. ............................ 134/42 |
| 5,908,822 A | | 6/1999 | Dishart |
| 7,498,296 B2 | | 3/2009 | Schweitzer et al. |
| 7,700,004 B2 | * | 4/2010 | Nappa et al. ................... 252/364 |
| 7,718,089 B2 | * | 5/2010 | Nappa et al. ................... 252/364 |
| 7,786,061 B2 | * | 8/2010 | Minor et al. ................... 510/177 |
| 2006/0094911 A1 | | 5/2006 | Rao et al. |
| 2006/0106263 A1 | | 5/2006 | Miller et al. |
| 2007/0096051 A1 | | 5/2007 | Nappa et al. |
| 2007/0098646 A1 | | 5/2007 | Nappa et al. |
| 2007/0100009 A1 | | 5/2007 | Creazzo et al. |
| 2007/0100010 A1 | | 5/2007 | Creazzo et al. |
| 2007/0100011 A1 | | 5/2007 | Creazzo et al. |
| 2007/0102021 A1 | | 5/2007 | Nappa et al. |
| 2007/0203045 A1 | | 8/2007 | Schweitzer et al. |
| 2007/0203046 A1 | | 8/2007 | Minor et al. |
| 2008/0011678 A1 | | 1/2008 | Knapp |
| 2009/0124524 A1 | | 5/2009 | Minor et al. |

OTHER PUBLICATIONS

CAS reg. No. 935476-91-8, May 21, 2007.*
F. Jeanneaux et al, "Addition Thermique Des IODO-1-Perfluoroalcanes Sur Les Perfluoroalkylethylenes", Journal of Fluorine Chemistry, 4 (1974) pp. 261-270.
World Meteorological Organization Global Ozone Research and Monitoring Project, Scientific Assessment of Ozone Depletion: 2002, "Source Gases". Report No. 47, Published Mar. 2003, pp. 1.28-1.31.
Zapevalov, et al, "A,A-Disubstituted Polyfluoralkenes", Russian Journal of Organic Chemistry, vol. 24 (1988), pp. 1466-1472.

* cited by examiner

*Primary Examiner* — Douglas McGinty

(57) ABSTRACT

This invention relates to cleaning compositions comprising unsaturated fluorinated hydrocarbons. The invention further relates to use of said cleaning compositions in methods to clean, degrease, deflux, dewater, and deposit fluorolubricant. The invention further relates to novel unsaturated fluorinated hydrocarbons and their use as cleaning compositions and in the methods listed above.

24 Claims, No Drawings

SOLVENT COMPOSITIONS COMPRISING UNSATURATED FLUORINATED HYDROCARBONS

CROSS REFERENCE(S) TO RELATED APPLICATION(S)

This application is a Divisional of U.S. application Ser. No. 11/591,650, filed Nov. 1, 2006, now U.S. Pat. No. 7,700,004, which claims the benefit of priority of U.S. Provisional Application 60/732,771, filed Nov. 1, 2005.

FIELD OF THE INVENTION

This invention relates to cleaning compositions comprising unsaturated fluorinated hydrocarbons. The invention further relates to use of said cleaning compositions in methods to clean, degrease, deflux, dewater, and deposit fluorolubricant. The invention further relates to novel unsaturated fluorinated hydrocarbons and their use as cleaning compositions and in the methods listed above.

BACKGROUND OF THE INVENTION

Chlorofluorocarbon (CFC) compounds have been used extensively in the area of semiconductor manufacture to clean surfaces such as magnetic disk media. However, chlorine-containing compounds such as CFC compounds are considered to be detrimental to the Earth's ozone layer. In addition, many of the hydrofluorocarbons used to replace CFC compounds have been found to contribute to global warming. Therefore, there is a need to identify new environmentally safe solvents for cleaning applications, such as removing residual flux, lubricant or oil contaminants, and particles. There is also a need for identification of new solvents for deposition of fluorolubricants and for drying or dewatering of substrates that have been processed in aqueous solutions.

The present invention provides new compositions comprising unsaturated fluorinated hydrocarbons. These compositions have utility in many of the applications formerly served by CFC compounds. The compositions of the present invention possess some or all of the desired properties of little or no environmental impact, ability to dissolve oils, greases or lubricants (in particular fluorine-containing lubricants), non-flammability, and ability to dissolve surfactant compounds used in methods for drying or dewatering.

SUMMARY OF THE INVENTION

Disclosed herein are novel methods of using a composition comprising at least one unsaturated fluorinated hydrocarbon selected from the group consisting of: compounds having the formula E- or Z—$R^1CH=CHR^2$, wherein $R^1$ and $R^2$ are, independently, $C_1$ to $C_6$ perfluoroalkyl groups, and unsaturated fluorinated hydrocarbons selected from the group consisting of $(CF_3)_2CFCH=CH_2$, $CF_3CF_2CF_2CH=CH_2$, $CH_2=CFCF_2CF_2CHF_2$, $CF_2=CHCF_2CH_2CF_3$, $CF_3CF=C(CF_3)(CH_3)$, $CH_2=CFCH(CF_3)_2$, $CHF=CHCH(CF_3)_2$, $CH_2FCH=C(CF_3)_2$, $CH_3CF=C(CF_3)_2$, $(CF_3)_2C=CHCH_3$, $CHF_2CF_2CF=CFCH_3$, $C_2F_5CF=CHCH_3$, $CF_3C(CH_3)=CHCF_3$, $CH_2=CHCF_2CHFCF_3$, $CH_2=C(CF_3)CH_2CF_3$, $CF_3CH=CFCH_2CH_3$, $CF_3CH=C(CH_3)_2$, $CF_3(CF_2)_3CF=CF_2$, $CF_3CF_2CF=CFCF_2CF_3$, $(CF_3)_2C=C(CF_3)_2$, $(CF_3)_2CFCF=CFCF_3$, $(CF_3)_2C=CHC_2F_5$, $(CF_3)_2CFCF=CHCF_3$, $CF_3CF_2CF_2CF_2CH=CH_2$, $CH_2=CHC(CF_3)_3$, $(CF_3)_2C=C(CH_3)(CF_3)$, $CH_2=CFCF_2CH(CF_3)_2$, $CF_3CF=C(CH_3)CF_2CF_3$, $CF_3CH=CHCH(CF_3)_2$, $(CF_3)_2CFCF=CHCH_3$, $CH_2=CHCF_2CF_2CHF_2$, $CH_2=C(CF_3)CH_2C_2F_5$, $CF_3CF_2CF_2CH=CHCH_3$, $CF_3CF_2CF=CFCH_3$, $CF_3CF=CFC_2H_5$, $CF_3CF=CHCH(CF_3)(CH_3)$, $(CF_3)_2C=CFC_2H_5$, $(CH_3)_2C=CFCF_2CF_3$, $CF_3CF=CFCF_2CF_2C_2F_5$, $CF_3CH=CFCF_2CF_2C_2F_5$, $CF_3CF_2CH=CFCF_2C_2F_5$, $CF_3CF_2CF=CHCF_2C_2F_5$, $CF_3CF_2CF_2CF_2CF=CHCH_3$, $CF_3CF_2CF_2CF=CHCH_2CH_3$, $(CH_3)_2C=CFCF_2CF_2CF_3$, cyclo-$CF_2CH=CHCF_2CF_2CF_2—$, cyclo-$CF_2CF=CFCF_2CF_2CF_2—$, $CF_2=CHCF_2Br$, $CF_2=CFCBrH_2$, $CHF=CBrCF_3$, $CHF=CHCBrF_2$, $CHF=CBrCHF_2$, $CHBr=CFCF_3$, $CHBr=CHCF_3$, $CH2=CBrCF_3$, $CH_2CFCBrF_2$, $CFBr=CHCF_3$, $CFBr=CFCF_3$, $CH_2=CBrCF_2CF_3$, $CHBr=CHCF_2CF_3$, $CH_2=CHCF_2CF_2Br$, $CH_2=CHCBrFCF_3$, $CF_3CBr=CFCF_3$, $CH_3CBr=CHCF_3$, $CF_3CBr=CHCH_3$, $(CF_3)_2C=CHBr$, $CF_3CF=CBrCF_2CF_3$, $CHF_2CBr=CFC_2F_5$, $CF_2=CBrCHFC_2F_5$, $CHBr=CF(CF_2)_2CHF_2$, $CH_2=CBrCF_2C_2F_5$, $CF_2=CHCF_2CH_2CBrF_2$, $(CF_3)_2CFCBr=CH_2$, $CF_2=C(CH_2Br)CF_3$, $CH_2=C(CBrF_2)CF_3$, $(CF_3)_2CHCH=CHBr$, $(CF_3)_2C=CHCH_2Br$, $CH_2=CHCF(CF_3)CBrF_2$, $CF_3CF_2CF_2CBr=CH_2$, $CF_3(CF_2)_3CBr=CH_2$, $CHCl=CFCClF_2$, $CHCl=CClCF_3$, $CHCl=CHCH_2F$, $CHCl=CFCH_3$, $CH_2=CClCH_2F$, $CHF=CClCH_3$, $CH_2=CClCClF_2$, $CH_2=CFCCl_2F$, $CHCl=CClCHF_2$, $CHCl=CHCClF_2$, $CHF=CClCHClF$, $CCl_2=CFCH_3$, $CH_2=CClCHClF$, $CH_2=C(CHF_2)CClF_2$, $CH_2=CHCF_2CHClF$, $CHCl=C(CH_3)CF_3$, $CH_2=CHCHClCF_3$, $CH_3CF=CHCClF_2$, $CH_2=CClCF_2CF_3$, $CHCl=CHCF_2CF_3$, $CH_2=CHCF_2CF_2Cl$, $CH_2=CHCClFCF_3$, $CH_3CCl=CHCF_3$, $CF_3CCl=CHCH_3$, $CH_2=CHCClFCHCl_2$, $CH_2=CClCClFCClF_2$, $CH_2=CClCH_2CClF_2$, $CH_2=CHCF_2CHCl_2$, $CH_2=CHCClFCClF_2$, $CCl_2=C(CH_3)CF_3$, $CCl_2=CHCH_2CF_3$, $CH_2=CFCClFCClF_2$, $CClF=CHC_2H_5$, $CHCl=CHCF_2CH_3$, $CH_2=CClCF_2CH_3$, $CH_3CH=CHCClF_2$, $(CF_3)_2C=CHCl$, $CF_3CH=C(CClF_2)CF_3$, $CHCl=CHCF_2CClFCF_3$, $CHCl=CHCF(CClF_2)CF_3$, $CF_3CF=CClCF_2CF_3$, $CHCl=CF(CF_2)_2CHF_2$, $CH_2=CClCF_2C_2F_5$, $CF_2=CHCF_2CH_2CClF_2$, $(CF_3)_2$ $CFCCl=CH_2$, $(CF_3)_2CHCH=CHCl$, $(CF_3)_2C=CHCH_2Cl$, $CH_2=CHCF(CF_3)CClF_2$, $CH_2=CClCF_2CF_2C_2F_5$, and $CHCl=CHCF_2CF_2C_2F_5$.

In one embodiment, the methods disclosed herein are methods of using a compound having the formula E- or Z—$R^1CH=CHR^2$, wherein $R^1$ and $R^2$ are, independently, $C_1$ to $C_6$ perfluoroalkyl groups, for cleaning an article or substrate.

In another embodiment is a method for depositing a fluorolubricant on a surface comprising: (a) combining a fluorolubricant and a solvent comprising an unsaturated fluorinated hydrocarbon selected from the group consisting of:
  (i) unsaturated fluorinated hydrocarbons having the formula E- or Z—$R^1CH=CHR^2$, wherein $R^1$ and $R^2$ are, independently, $C_1$ to $C_6$ perfluoroalkyl groups; and
  (ii) unsaturated fluorinated hydrocarbons selected from the group consisting of $(CF_3)_2CFCH=CH_2$, $CF_3CF_2CF_2CH=CH_2$, $CH_2=CFCF_2CF_2CHF_2$, $CF_2=CHCF_2CH_2CF_3$, $CF_3CF=C(CF_3)(CH_3)$, $CH_2=CFCH(CF_3)_2$, $CHF=CHCH(CF_3)_2$, $CH_2FCH=C(CF_3)_2$, $CH_3CF=C(CF_3)_2$, $(CF_3)_2C$ =CHCH$_3$, CHF$_2$CF$_2$CF=CFCH$_3$, C$_2$F$_5$CF=CHCH$_3$, CF$_3$C(CH$_3$)=CHCF$_3$, CH$_2$=CHCF$_2$CHFCF$_3$, CH$_2$=C(CF$_3$)CH$_2$CF$_3$, CF$_3$CH=CFCH$_2$CH$_3$, CF$_3$CH=C(CH$_3$)$_2$, CF$_3$(CF$_2$)$_3$CF=CF$_2$, CF$_3$CF$_2$CF=CFCF$_2$CF$_3$, (CF$_3$)$_2$C=C(CF$_3$)$_2$, (CF$_3$)$_2$CFCF=CFCF$_3$, (CF$_3$)$_2$C=CHC$_2$F$_5$, (CF$_3$)$_2$CFCF=CHCF$_3$, CF$_3$CF$_2$CF$_2$CF$_2$CH=CH$_2$, CH$_2$=CHC(CF$_3$)$_3$, (CF$_3$)$_2$C=C(CH$_3$)(CF$_3$), CH$_2$=CFCF$_2$CH(CF$_3$)$_2$, CF$_3$CF=C(CH$_3$)CF$_2$CF$_3$, CF$_3$CH=CHCH(CF$_3$)$_2$, (CF$_3$)$_2$CFCF=CHCH$_3$, CF$_3$CF$_2$CF$_2$CF=CHCH$_3$, CH$_2$=CHCF$_2$CF$_2$CF$_2$CHF$_2$, (CF$_3$)$_2$C=CHCF$_2$CH$_3$, CH$_2$=C(CF$_3$)CH$_2$C$_2$F$_5$, CF$_3$CF$_2$CF$_2$C(CH$_3$)=CH$_2$, CF$_3$CF$_2$CF$_2$CH=CHCH$_3$, CH$_2$=CHCH$_2$CF$_2$C$_2$F$_5$, CF$_3$CF$_2$CF=CFC$_2$H$_5$, CH$_2$=CHCH$_2$CF(CF$_3$)$_2$, CF$_3$CF=CHCH(CF$_3$)(CH$_3$), (CF$_3$)$_2$C=CFC$_2$H$_5$, (CH$_3$)$_2$C=CFCF$_2$CF$_3$, (CF$_3$)$_2$C=C(CH$_3$)$_2$, CF$_3$CF=CFCF$_2$CF$_2$C$_2$F$_5$, CF$_3$CF$_2$CF=CFCF$_2$C$_2$F$_5$, CF$_3$CH=CFCF$_2$CF$_2$C$_2$F$_5$, CF$_3$CF=CHCF$_2$CF$_2$C$_2$F$_5$, CF$_3$CF$_2$CH=CFCF$_2$C$_2$F$_5$, CF$_3$CF$_2$CF=CHCF$_2$C$_2$F$_5$, CF$_3$CF$_2$CF$_2$CF$_2$CF=CHCH$_3$, CF$_3$CF$_2$CF$_2$CF=CHCH$_2$CH$_3$, (CH$_3$)$_2$C=CFCF$_2$CF$_2$CF$_3$, cyclo-CF$_2$CH=CHCF$_2$CF$_2$CF$_2$—, cyclo-CF$_2$CF=CFCF$_2$CF$_2$CF$_2$—, CF$_2$=CHCF$_2$Br, CF$_2$=CFCBrH$_2$, CHF=CBrCF$_2$, CHF=CHCBrF$_2$, CHF=CBrCHF$_2$, CHBr=CFCF$_3$, CHBr=CHCF$_3$, CH2=CBrCF$_3$, CH$_2$CFCBrF$_2$, CFBr=CHCF$_3$, CFBr=CFCF$_3$, CH$_2$=CBrCF$_2$CF$_3$, CHBr=CHCF$_2$CF$_3$, CH$_2$=CHCF$_2$CF$_2$Br, CH$_2$=CHCBrFCF$_3$, CF$_3$CBr=CFCF$_3$, CH$_3$CBr=CHCF$_3$, CF$_3$CBr=CHCH$_3$, (CF$_3$)$_2$C=CHBr, CF$_3$CF=CBrCF$_2$CF$_3$, CHF$_2$CBr=CFC$_2$F$_5$, CF$_2$=CBrCHFC$_2$F$_5$, CHBr=CF(CF$_2$)$_2$CHF$_2$, CH$_2$=CBrCF$_2$C$_2$F$_5$, CF$_2$=CHCF$_2$CH$_2$CBrF$_2$, (CF$_3$)$_2$CFCBr=CH$_2$, CF$_2$=C(CH$_2$Br)CF$_3$, CH$_2$=C(CBrF$_2$)CF$_3$, (CF$_3$)$_2$CHCH=CHBr, (CF$_3$)$_2$C=CHCH$_2$Br, CH$_2$=CHCF(CF$_3$)CBrF$_2$, CF$_3$CF$_2$CF$_2$CBr=CH$_2$, CF$_3$(CF$_2$)$_3$CBr=CH$_2$, CHCl=CFCClF$_2$, CHCl=CClCF$_3$, CHCl=CHCH$_2$F, CHCl=CFCH$_3$, CH$_2$=CClCH$_2$F, CHF=CClCH$_3$, CH$_2$=CClCClF$_2$, CH$_2$=CFCCl$_2$F, CHCl=CClCHF$_2$, CHCl=CHCClF$_2$, CHF=CClCHClF, CCl$_2$=CFCH$_3$, CH$_2$=CClCHClF, CH$_2$=C(CHF$_2$)CClF$_2$, CH$_2$=CHCF$_2$CHClF, CHCl=C(CH$_3$)CF$_3$, CH$_2$=CHCHClCF$_3$, CH$_3$CF=CHCClF$_2$, CH$_2$=CClCF$_2$CF$_3$, CHCl=CHCF$_2$CF$_3$, CH$_2$=CHCF$_2$CF$_2$Cl, CH$_2$=CHCClFCF$_3$, CH$_3$CCl=CHCF$_3$, CF$_3$CCl=CHCH$_3$, CH$_2$=CHCClFCHCl$_2$, CH$_2$=CClCClFCClF$_2$, CH$_2$=CClCH$_2$CClF$_2$, CH$_2$=CHCF$_2$CHCl$_2$, CH$_2$=CHCClFCClF$_2$, CCl$_2$=C(CH$_3$)CF$_3$, CCl$_2$=CHCH$_2$CF$_3$, CH$_2$=CFCClFCClF$_2$, CClF=CHC$_2$H$_5$, CHCl=CHCF$_2$CH$_3$, CH$_2$=CClCF$_2$CH$_3$, CH$_3$CH=CHCClF$_2$, (CF$_3$)$_2$C=CHCl, CF$_3$CH=C(CClF$_2$)CF$_3$, CHCl=CHCF$_2$CClFCF$_3$, CHCl=CHCF(CClF$_2$)CF$_3$, CF$_3$CF=CClCF$_2$CF$_3$, CHCl=CF(CF$_2$)$_2$CHF$_2$, CH$_2$=CClCF$_2$C$_2$F$_5$, CF$_2$=CHCF$_2$CH$_2$CClF$_2$, (CF$_3$)$_2$CFCCl=CH$_2$, (CF$_3$)$_2$CHCH=CHCl, (CF$_3$)$_2$C=CHCH$_2$Cl, CH$_2$=CHCF(CF$_3$)CClF$_2$, CH$_2$=CClCF$_2$CF$_2$C$_2$F$_5$, and CHCl=CHCF$_2$CF$_2$C$_2$F$_5$, to form a lubricant-solvent combination;

(b) contacting the combination of lubricant-solvent with the surface; and (c) evaporating the solvent from the surface to form a fluorolubricant coating on the surface.

In yet another embodiment is a process for removing at least a portion of water from the surface of a wetted substrate, said process comprising:

a) contacting the substrate with the compositions of the present invention further comprising surfactant, and then b) removing the substrate from contact with said composition.

In yet another embodiment is a composition comprising an unsaturated fluorinated hydrocarbon having the formula R$^1$CH=CHR$^2$, wherein R$^1$ and R$^2$ are, independently, C$_1$ to C$_6$ perfluoroalkyl groups.

In yet another embodiment is a composition comprising an unsaturated fluorinated hydrocarbon selected from the group consisting of CH$_2$=CClCF$_2$CF$_3$, CHCl=CHCF$_2$CF$_3$, CHCl=CHCF$_2$CF$_2$C$_2$F$_5$ and CHBr=CHCF$_2$CF$_3$.

Other objects and advantages of the present invention will become apparent to those skilled in the art upon reference to the detailed description that hereinafter follows.

DETAILED DESCRIPTION OF THE INVENTION

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Applicants specifically incorporate the entire content of all cited references in this disclosure. Applicants also incorporate by reference the co-owned Provisional applications 60/732,396, filed Nov. 1, 2005, 60/732,090, filed Nov. 1, 2005, 60/732,292, filed Nov. 1, 2005 and 60/732,581, filed Nov. 1, 2005.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In one embodiment, the present invention provides compounds having the formula E- or Z—$R^1CH=CHR^2$ (Formula I), wherein $R^1$ and $R^2$ are, independently, $C_1$ to $C_6$ perfluoroalkyl groups. Examples of $R^1$ and $R^2$ groups include, but are not limited to, $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)_2$, $C(CF_3)_2C_2F_5$, $CF_2CF_2CF_2CF_2CF_2CF_3$, $CF(CF_3)$ $CF_2CF_2C_2F_5$, and $C(CF_3)_2CF_2C_2F_5$. Exemplary, non-limiting Formula I compounds are presented in Table 1.

TABLE 1

| Code | Structure | Chemical Name |
|---|---|---|
| F11E | $CF_3CH=CHCF_3$ | 1,1,1,4,4,4-hexafluorobut-2-ene |
| F12E | $CF_3CH=CHC_2F_5$ | 1,1,1,4,4,5,5,5-octafluoropent-2-ene |
| F13E | $CF_3CH=CHCF_2C_2F_5$ | 1,1,1,4,4,5,5,6,6,6-decafluorohex-2-ene |
| F13iE | $CF_3CH=CHCF(CF_3)_2$ | 1,1,1,4,5,5,5-heptafluoro-4-(trifluoromethyl)pent-2-ene |
| F22E | $C_2F_5CH=CHC_2F_5$ | 1,1,1,2,2,5,5,6,6,6-decafluorohex-3-ene |
| F14E | $CF_3CH=CH(CF_2)_3CF_3$ | 1,1,1,4,4,5,5,6,6,7,7,7-dodecafluorohept-2-ene |
| F14iE | $CF_3CH=CHCF_2CF—(CF_3)_2$ | 1,1,1,4,4,5,6,6,6-nonafluoro-5-(trifluoromethyl)hex-2-ene |
| F14sE | $CF_3CH=CHCF(CF_3)—C_2F_5$ | 1,1,1,4,5,5,6,6,6-nonfluoro-4-(trifluoromethyl)hex-2-ene |
| F14tE | $CF_3CH=CHC(CF_3)_3$ | 1,1,1,5,5,5-hexafluoro-4,4-bis(trifluoromethyl)pent-2-ene |
| F23E | $C_2F_5CH=CHCF_2C_2F_5$ | 1,1,1,2,2,5,5,6,6,7,7,7-dodecafluorohept-3-ene |
| F23iE | $C_2F_5CH=CHCF(CF_3)_2$ | 1,1,1,2,2,5,6,6,6-nonafluoro-5-(trifluoromethyl)hex-3-ene |
| F15E | $CF_3CH=CH(CF_2)_4CF_3$ | 1,1,1,4,4,5,5,6,6,7,7,8,8,8-tetradecafluorooct-2-ene |
| F15iE | $CF_3CH=CH—CF_2CF_2CF(CF_3)_2$ | 1,1,1,4,4,5,5,6,7,7,7-undecafluoro-6-(trifluoromethyl)hept-2-ene |
| F15tE | $CF_3CH=CH—C(CF_3)_2C_2F_5$ | 1,1,1,5,5,6,6,6-octafluoro-4,4-bis(trifluoromethyl)hex-2-ene |
| F24E | $C_2F_5CH=CH(CF_2)_3CF_3$ | 1,1,1,2,2,5,5,6,6,7,7,8,8,8-tetradecafluorooct-3-ene |
| F24iE | $C_2F_5CH=CHCF_2CF—(CF_3)_2$ | 1,1,1,2,2,5,5,6,7,7,7-undecafluoro-6-(trifluoromethyl)hept-3-ene |
| F24sE | $C_2F_5CH=CHCF(CF_3)—C_2F_5$ | 1,1,1,2,2,5,5,6,6,7,7,7-undecafluoro-5-(trifluoromethyl)hept-3-ene |
| F24tE | $C_2F_5CH=CHC(CF_3)_3$ | 1,1,1,2,2,6,6,6-octafluoro-5,5-bis(trifluoromethyl)hex-3-ene |
| F33E | $C_2F_5CF_2CH=CH—CF_2C_2F_5$ | 1,1,1,2,2,3,3,6,6,7,7,8,8,8-tetradecafluorooct-4-ene |
| F3i3iE | $(CF_3)_2CFCH=CH—CF(CF_3)_2$ | 1,1,1,2,5,6,6,6-octafluoro-2,5-bis(trifluoromethyl)hex-3-ene |
| F33iE | $C_2F_5CF_2CH=CH—CF(CF_3)_2$ | 1,1,1,2,5,5,6,6,7,7,7-undecafluoro-2-(trifluoromethyl)hept-3-ene |
| F16E | $CF_3CH=CH(CF_2)_5CF_3$ | 1,1,1,4,4,5,5,6,6,7,7,8,8,,9,9,9-hexadecafluoronon-2-ene |
| F16sE | $CF_3CH=CHCF(CF_3)(CF_2)_2C_2F_5$ | 1,1,1,4,5,5,6,6,7,7,8,8,8-tridecafluoro-4-(trifluoromethyl)hept-2-ene |
| F16tE | $CF_3CH=CHC(CF_3)_2CF_2C_2F_5$ | 1,1,1,6,6,6-octafluoro-4,4-bis(trifluoromethyl)hept-2-ene |
| F25E | $C_2F_5CH=CH(CF_2)_4CF_3$ | 1,1,1,2,2,5,5,6,6,7,7,8,8,9,9,9-hexadecafluoronon-3-ene |
| F25iE | $C_2F_5CH=CH—CF_2CF_2CF(CF_3)_2$ | 1,1,1,2,2,5,5,6,6,7,8,8,8-tridecafluoro-7-(trifluoromethyl)oct-3-ene |
| F25tE | $C_2F_5CH=CH—C(CF_3)_2C_2F_5$ | 1,1,1,2,2,6,6,7,7,7-decanfluoro-5,5-bis(trifluoromethyl)hept-3-ene |
| F34E | $C_2F_5CF_2CH=CH—(CF_2)_3CF_3$ | 1,1,1,2,2,3,3,6,6,7,7,8,8,9,9,9-hexadecafluoronon-4-ene |
| F34iE | $C_2F_5CF_2CH=CH—CF_2CF(CF_3)_2$ | 1,1,1,2,2,3,3,6,6,7,8,8,8-tridecafluoro-7-(trifluoromethyl)oct-4-ene |
| F34sE | $C_2F_5CF_2CH=CH—CF(CF_3)C_2F_5$ | 1,1,1,2,2,3,3,6,7,7,8,8,8-tridecafluoro-6-(trifluoromethyl)oct-4-ene |
| F34tE | $C_2F_5CF_2CH=CH—C(CF_3)_3$ | 1,1,1,5,5,6,6,7,7,7-decafluoro-2,2-bis(trifluoromethyl)hept-3-ene |
| F3i4E | $(CF_3)_2CFCH=CH—(CF_2)_3CF_3$ | 1,1,1,2,5,5,6,6,7,7,8,8,8-tridecafluoro-2(trifluoromethyl)oct-3-ene |
| F3i4iE | $(CF_3)_2CFCH=CH—CF_2CF(CF_3)_2$ | 1,1,1,2,5,5,6,7,7,7-decafluoro-2,6-bis(trifluoromethyl)hept-3-ene |
| F3i4sE | $(CF_3)_2CFCH=CH—CF(CF_3)C_2F_5$ | 1,1,1,2,5,6,6,7,7,7-decafluoro-2,5-bis(trifluoromethyl)hept-3-ene |
| F3i4tE | $(CF_3)_2CFCH=CH—C(CF_3)_3$ | 1,1,1,2,6,6,6-heptafluoro-2,5,5-tris(trifluoromethyl)hex-3-ene |
| F26E | $C_2F_5CH=CH(CF_2)_5CF_3$ | 1,1,1,2,2,5,5,6,6,7,7,8,8,9,9,10,10,10-octadecafluorodec-3-ene |
| F26sE | $C_2F_5CH=CHCF(CF_3)(CF_2)_2C_2F_5$ | 1,1,1,2,2,5,6,6,7,7,8,8,9,9,9-pentadecafluoro-5-(trifluoromethyl)non-3-ene |
| F26tE | $C_2F_5CH=CHC(CF_3)_2CF_2C_2F_5$ | 1,1,1,2,2,6,6,7,7,8,8,8-dodecafluoro-5,5-bis(trifluoromethyl)oct-3-ene |
| F35E | $C_2F_5CF_2CH=CH—(CF_2)_4CF_3$ | 1,1,1,2,2,3,3,6,6,7,7,8,8,9,9,10,10,10-octadecafluorodec-4-ene |

TABLE 1-continued

| Code | Structure | Chemical Name |
|---|---|---|
| F35iE | $C_2F_5CF_2CH=CH—CF_2CF_2CF(CF_3)_2$ | 1,1,1,2,2,3,3,6,6,7,7,8,9,9,9-pentadecafluoro-8-(trifluoromethyl)non-4-ene |
| F35tE | $C_2F_5CF_2CH=CH—C(CF_3)_2C_2F_5$ | 1,1,1,2,2,3,3,7,7,8,8,8-dodecafluoro-6,6-bis(trifluoromethyl)oct-4-ene |
| F3i5E | $(CF_3)_2CFCH=CH—(CF_2)_4CF_3$ | 1,1,1,2,5,5,6,6,7,7,8,8,9,9,9-pentadecafluoro-2-(trifluoromethyl)non-3-ene |
| F3i5iE | $(CF_3)_2CFCH=CH—CF_2CF_2CF(CF_3)_2$ | 1,1,1,2,5,5,6,6,7,8,8,8-dodecafluoro-2,7-bis(trifluoromethyl)oct-3-ene |
| F3i5tE | $(CF_3)_2CFCH=CH—C(CF_3)_2C_2F_5$ | 1,1,1,2,6,6,7,7,7-nonafluoro-2,5,5-tris(trifluoromethyl)hept-3-ene |
| F44E | $CF_3(CF_2)_3CH=CH—(CF_2)_3CF_3$ | 1,1,1,2,2,3,3,4,4,7,7,8,8,9,9,10,10,10-octadecafluorodec-5-ene |
| F44iE | $CF_3(CF_2)_3CH=CH—CF_2CF(CF_3)_2$ | 1,1,1,2,3,3,6,6,7,7,8,8,9,9,9-pentadecafluoro-2-(trifluoromethyl)non-4-ene |
| F44sE | $CF_3(CF_2)_3CH=CH—CF(CF_3)C_2F_5$ | 1,1,1,2,2,3,6,6,7,7,8,8,9,9,9-pentadecafluoro-3-(trifluoromethyl)non-4-ene |
| F44tE | $CF_3(CF_2)_3CH=CH—C(CF_3)_3$ | 1,1,1,5,5,6,6,7,7,8,8,8-dodecafluoro-2,2-bis(trifluoromethyl)oct-3-ene |
| F4i4iE | $(CF_3)_2CFCF_2CH=CH—CF_2CF(CF_3)_2$ | 1,1,1,2,3,3,6,6,7,8,8,8-dodecafluoro-2,7-bis(trifluoromethyl)oct-4-ene |
| F4i4sE | $(CF_3)_2CFCF_2CH=CH—CF(CF_3)C_2F_5$ | 1,1,1,2,3,3,6,7,7,8,8,8-dodecafluoro-2,6-bis(trifluoromethyl)oct-4-ene |
| F4i4tE | $(CF_3)_2CFCF_2CH=CH—C(CF_3)_3$ | 1,1,1,5,5,6,6,7,7,7-nonafluoro-2,2,6-tris(trifluoromethyl)hept-3-ene |
| F4s4sE | $C_2F_5CF(CF_3)CH=CH—CF(CF_3)C_2F_5$ | 1,1,1,2,2,3,6,7,7,8,8,8-dodecafluoro-3,6-bis(trifluoromethyl)oct-4-ene |
| F4s4tE | $C_2F_5CF(CF_3)CH=CH—C(CF_3)_3$ | 1,1,1,5,6,6,7,7,7-nonafluoro-2,2,5-tris(trifluoromethyl)hept-3-ene |
| F4t4tE | $(CF_3)_3CCH=CH—C(CF_3)_3$ | 1,1,1,6,6,6-hexafluoro-2,2,5,5-tetrakis(trifluoromethyl)hex-3-ene |

In one embodiment, compounds of Formula I may be prepared by contacting a perfluoroalkyl iodide of the formula $R^1I$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. In another embodiment, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^2I$ with a perfluoroalkyltrihydroolefin of the formula $R^1CH=CH_2$.

In one embodiment, said contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include those fabricated from stainless steels, in particular of the austenitic type, and the well-known high nickel alloys such as Monel® nickel-copper alloys, Hastelloy® nickel based alloys and Inconel® nickel-chromium alloys.

In another embodiment, the reaction may take be conducted in semi-batch mode in which the perfluoroalkyltrihydroolefin reactant is added to the perfluoroalkyl iodide reactant by means of a suitable addition apparatus such as a pump at the reaction temperature.

In one embodiment, the ratio of perfluoroalkyl iodide to perfluoroalkyltrihydroolefin is between about 1:1 to about 4:1. In another embodiment, the ratio of perfluoroalkyl iodide to perfluoroalkyltrihydroolefin is between from about 1.5:1 to 2.5:1. Ratios less than 1.5:1 tend to result in large amounts of the 2:1 adduct as reported by Jeanneaux, et. al. in Journal of Fluorine Chemistry, Vol. 4, pages 261-270 (1974).

In one embodiment, the temperature for contacting of said perfluoroalkyl iodide with said perfluoroalkyltrihydroolefin is within the range of about 150° C. to about 300° C. In another embodiment, the temperature is from about 170° C. to about 250° C. In yet another embodiment, the temperature is from about 180° C. to about 230° C.

In one embodiment, the contact time for the reaction of the perfluoroalkyl iodide with the perfluoroalkyltrihydroolefin is from about 0.5 hour to about 18 hours. In another embodiment, the contact time is from about 4 to about 12 hours.

In yet another embodiment, the contacting of a perfluoroalkyliodide with a perfluoroalkyltrihydroolefin takes place in the presence of a catalyst. In one embodiment, a suitable catalyst is a Group VIII transition metal complex. Representative Group VIII transition metal complexes include, without limitation, zero valent $NiL_4$ complexes, wherein the ligand, L, can be a phosphine ligand, a phosphite ligand, a carbonyl ligand, an isonitrile ligand, an alkene ligand, or a combination thereof. In one such embodiment, the $Ni(0)L_4$ complex is a $NiL_2(CO)_2$ complex. In one particular embodiment, the Group VIII transition metal complex is bis(triphenyl phosphine)nickel(0) dicarbonyl. In one embodiment, the ratio of perfluoroalkyl iodide to perfluoroalkyltrihydroolefin is between about 3:1 to about 8:1. In one embodiment, the temperature for contacting of said perfluoroalkyl iodide with said perfluoroalkyltrihydroolefin in the presence of a catalyst, is within the range of about 80° C. to about 130° C. In another embodiment, the temperature is from about 90° C. to about 120° C.

In one embodiment, the contact time for the reaction of the perfluoroalkyl iodide with the perfluoroalkyltrihydroolefin in the presence of a catalyst is from about 0.5 hour to about 18 hours. In another embodiment, the contact time is from about 4 to about 12 hours.

In one embodiment, the trihydroiodoperfluoroalkane prepared by reaction of the perfluoroalkyl iodide with the perfluoroalkyltrihydroolefin may be used directly in the dehydroiodination step. In another embodiment, the trihydroperfluoroalkane is recovered and purified by distillation prior to the dehydroiodination step.

In one embodiment, the dehydroiodination step is carried out by contacting the trihydroiodoperfluoroalkane with a basic substance. In one embodiment, basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. In another embodiment, the basic substance is sodium hydroxide or potassium hydroxide.

In one embodiment, contacting of the trihydroiodoperfluoroalkane with a basic substance may take place in the liquid phase. In another embodiment, the contacting in the liquid phase further takes place in the presence of a solvent capable of dissolving at least a portion of both reactants. In one embodiment, solvents suitable for the dehydroiodination step include one or more polar organic solvents such as alcohols (e.g., methanol, ethanol, n-propanol, isopropanol, n-butanol, isobutanol, and tertiary butanol), nitriles (e.g., acetonitrile, propionitrile, butyronitrile, benzonitrile, or adiponitrile), dimethyl sulfoxide, N,N-dimethylformamide, N,N-dimethylacetamide, or sulfolane. In one embodiment, the solvent is chosen based on the boiling point of the product and the ease of separation of traces of the solvent from the product during purification. In one embodiment, ethanol or isopropanol are good solvents for the reaction.

In one embodiment, the dehydroiodination reaction is carried out by addition of one of the reactants (either the basic substance or the trihydroiodoperfluoroalkane) to the other reactant in a suitable reaction vessel. Said reaction vessel may be fabricated from glass, ceramic, or metal and is preferably agitated with an impeller or stirring mechanism.

In one embodiment, the temperature for the dehydroiodination reaction is from about 10° C. to about 100° C. In another embodiment, the temperature for the dehydroiodination reaction is from about 20° C. to about 70° C. In one embodiment, the dehydroiodination reaction is carried out at ambient pressure. In another embodiment, the dehydroiodination reaction is carried out at reduced or elevated pressure. In one embodiment of the dehydroiodination reaction the compound of Formula I is distilled out of the reaction vessel as it is formed.

In another embodiment, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. In one such embodiment, the phase transfer catalyst includes quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), or cyclic polyether compounds known in the art as crown ethers (e.g., 18-crown-6 and 15-crown-5).

In yet another embodiment, the dehydroiodination reaction is conducted in the absence of solvent by adding the trihydroiodoperfluoroalkane to a solid or liquid basic substance.

In one embodiment, the reaction time for the dehydroiodination reactions are from about 15 minutes to about six hours or more depending on the solubility of the reactants. In another embodiment, the dehydroiodination reaction requires from about 30 minutes to about three hours for completion.

In one embodiment, the compound of formula I is recovered from the dehydroiodination reaction mixture by phase separation after addition of water. In another embodiment, the compound of formula I is recovered from the dehydroiodination reaction mixture by distillation. In yet another embodiment, the compound of formula I is recovered from the dehydroiodination reaction mixture by a combination of phase separation after addition of water and distillation.

In one embodiment, the compositions of the present invention may comprise a single compound of Formula I, for example, one of the compounds in Table 1. In another embodiment, the compositions may comprise a combination of compounds of Formula I.

Many of the compounds of Formula I exist as different configurational isomers or stereoisomers. When the specific isomer is not designated, the present invention is intended to include all single configurational isomers, single stereoisomers, or any combination thereof. For instance, F11E is meant to represent the E-isomer, Z-isomer, or any combination or mixture of both isomers in any ratio. Another example is F33E, by which is represented the E-isomer, Z-isomer, or any combination or mixture of both isomers in any ratio.

In addition to the inventive compounds described above, unsaturated fluorinated hydrocarbons presented in Table 2 can be used as cleaning compositions, or also as cleaning agents, for cleaning surfaces or substrates.

TABLE 2

| Name | Structure | Chemical name |
| --- | --- | --- |
| HFC-1447fzy | $(CF_3)_2CFCH=CH_2$ | 3,4,4,4-tetrafluoro-3-(trifluoromethyl)-1-butene |
| HFC-1447fz | $CF_3CF_2CF_2CH=CH_2$ | 3,3,4,4,5,5,5-heptafluoro-1-pentene |
| HFC-1447fycc | $CH_2=CFCF_2CF_2CHF_2$ | 2,3,3,4,4,5,5-heptafluoro-1-pentene |
| HFC-1447czcf | $CF_2=CHCF_2CH_2CF_3$ | 1,1,3,3,5,5,5-heptafluoro-1-pentene |
| HFC-1447mytm | $CF_3CF=C(CF_3)(CH_3)$ | 1,1,1,2,4,4,4-heptafluoro-3-methyl-2-butene |
| HFC-1447fyz | $CH_2=CFCH(CF_3)_2$ | 2,4,4,4-tetrafluoro-3-(trifluoromethyl)-1-butene |
| HFC-1447ezz | $CHF=CHCH(CF_3)_2$ | 1,4,4,4-tetrafluoro-3-(trifluoromethyl)-1-butene |
| HFC-1447qzt | $CH_2FCH=C(CF_3)_2$ | 1,4,4,4-tetrafluoro-3-(trifluoromethyl)-2-butene |
| HFC-1447syt | $CH_3CF=C(CF_3)_2$ | 2,4,4,4-tetrafluoro-3-(trifluoromethyl)-2-butene |

TABLE 2-continued

| Name | Structure | Chemical name |
| --- | --- | --- |
| HFC-1456szt | $(CF_3)_2C=CHCH_3$ | 3-(trifluoromethyl)-4,4,4-trifluoro-2-butene |
| HFC-1456pcyy | $CHF_2CF_2CF=CFCH_3$ | 2,3,4,4,5,5,5-hexafluoro-2-pentene |
| HFC-1456szy | $CF_3CF_2CF=CHCH_3$ | 3,4,4,5,5,5-hexafluoro-2-pentene |
| HFC-1456mstz | $CF_3C(CH_3)=CHCF_3$ | 1,1,1,4,4,4-hexafluoro-2-methyl-2-butene |
| HFC-1456fzce | $CH_2=CHCF_2CHFCF_3$ | 3,3,4,5,5,5-hexafluoro-1-pentene |
| HFC-1456ftmf | $CH_2=C(CF_3)CH_2CF_3$ | 4,4,4-trifluoro-2-(trifluoromethyl)-1-butene |
| HFC-1474mzyf | $CF_3CH=CFCH_2CH_3$ | 1,1,1,3-tetrafluoro-2-pentene |
| HFC-1483mzt | $CF_3CH=C(CH_3)_2$ | 1,1,1-trifluoro-3-methyl-2-butene |
| FC-151-12c | $CF_3(CF_2)_3CF=CF_2$ | 1,1,2,3,3,4,4,5,5,6,6,6-dodecafluoro-1-hexene (or perfluoro-1-hexene) |
| FC-151-12mcy | $CF_3CF_2CF=CFCF_2CF_3$ | 1,1,1,2,2,3,4,5,5,6,6,6-dodecafluoro-3-hexene (or perfluoro-3-hexene) |
| FC-151-12mmtt | $(CF_3)_2C=C(CF_3)_2$ | 1,1,1,4,4,4-hexafluoro-2,3-bis(trifluoromethyl)-2-butene |
| FC-151-12mmzz | $(CF_3)_2CFCF=CFCF_3$ | 1,1,1,2,3,4,5,5,5-nonafluoro-4-(trifluoromethyl)-2-pentene |
| HFC-152-11mmtz | $(CF_3)_2C=CHC_2F_5$ | 1,1,1,4,4,5,5,5-octafluoro-2-(trifluoromethyl)-2-pentene |
| HFC-152-11mmyyz | $(CF_3)_2CFCF=CHCF_3$ | 1,1,1,3,4,5,5,5-octafluoro-4-(trifluoromethyl)-2-pentene |
| PFBE (or HFC-1549fz) | $CF_3CF_2CF_2CF_2CH=CH_2$ | 3,3,4,4,5,5,6,6,6-nonafluoro-1-hexene (or perfluorobutylethylene) |
| HFC-1549fztmm | $CH_2=CHC(CF_3)_3$ | 4,4,4-trifluoro-3,3-bis(trifluoromethyl)-1-butene |
| HFC-1549mmtts | $(CF_3)_2C=C(CH_3)(CF_3)$ | 1,1,1,4,4,4-hexafluoro-3-methyl-2-(trifluoromethyl)-2-butene |
| HFC-1549fycz | $CH_2=CFCF_2CH(CF_3)_2$ | 2,3,3,5,5,5-hexafluoro-4-(trifluoromethyl)-1-pentene |
| HFC-1549myts | $CF_3CF=C(CH_3)CF_2CF_3$ | 1,1,1,2,4,4,5,5,5-nonafluoro-3-methyl-2-pentene |
| HFC-1549mzzz | $CF_3CH=CHCH(CF_3)_2$ | 1,1,1,5,5,5-hexafluoro-4-(trifluoromethyl)-2-pentene |
| HFC-1558szcc | $(CF_3)_2CFCF=CHCH_3$ | 3,4,5,5,5-pentafluoro-4-trifluoromethyl-2-butene |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| HFC-1576ssty | $(CH_3)_2C=CFCF_2CF_3$ | 3,4,4,5,5,5-hexafluoro-2-methyl-2-pentene |
| HFC-1576mmtt | $(CF_3)_2C=C(CH_3)_2$ | 4-methyl-1,1,1-trifluoro-2-trifluoromethyl-2-butene |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFC-162-13mzy | $CF_3CH=CFCF_2CF_2C_2F_5$ | 1,1,1,3,4,4,5,5,6,6,7,7,7-tridecafluoro-2-heptene |
| HFC-162-13myz | $CF_3CF=CHCF_2CF_2C_2F_5$ | 1,1,1,2,4,4,5,5,6,6,7,7,7-tridecafluoro-2-heptene |
| HFC-162-13mczy | $CF_3CF_2CH=CFCF_2C_2F_5$ | 1,1,1,2,2,4,5,5,6,6,7,7,7-tridecafluoro-3-heptene |
| HFC-162-13mcyz | $CF_3CF_2CF=CHCF_2C_2F_5$ | 1,1,1,2,2,3,5,5,6,6,7,7,7-tridecafluoro-3-heptene |

TABLE 2-continued

| Name | Structure | Chemical name |
|---|---|---|
| HFC-1659szy | $CF_3CF_2CF_2CF_2CF=CHCH_3$ | 3,4,4,5,5,6,6,6-octafluoro-2-heptene |
| HFC-1678sfzy | $CF_3CF_2CF_2CF=CHCH_2CH_3$ | 4,5,5,6,6,7,7,7-octafluoro-3-heptene |
| HFC-1678ssty | $(CH_3)_2C=CFCF_2CF_2CF_3$ | 3,4,4,5,5,6,6,6-octafluoro-methyl-2-hexene |
| HFC-C1538zz | cyclo-$CF_2CH=CHCF_2CF_2CF_2$— | 3,3,4,4,5,5,6,6-octafluorocyclohexene |
| FC-C151-10y | cyclo-$CF_2CF=CFCF_2CF_2CF_2$— | 1,2,3,3,4,4,5,5,6,6-decafluorocyclohexene |

The compounds listed in Table 2 are available commercially or may be prepared by processes known in the art or as described herein.

In one embodiment, cleaning compositions can comprise a single compound as listed, for example, in Table 2. In another embodiment, cleaning compositions may comprise a combination of compounds from Table 2. In yet another embodiment, cleaning compositions may comprise a combination of compounds from Table 2 and one or more compounds of Formula I.

Many of the compounds in Table 2 exist as different configurational isomers or stereoisomers. When the specific isomer is not designated, the present invention is intended to include all single configurational isomers, single stereoisomers, or any combination thereof. For instance, 3,4,4,5,5,6,6,6-octafluoro-2-hexene (HFC-1558szy) is meant to represent the E-isomer, Z-isomer, or any combination or mixture of both isomers in any ratio. Another example is 1,1,1,2,2,4,5,5,6,6,7,7,7-tridecafluoro-3-heptene (HFC-162-13mczy), by which is represented the E-isomer, Z-isomer, or any combination or mixture of both isomers in any ratio.

In addition to the inventive compounds described above, the bromine-containing unsaturated fluorinated hydrocarbons presented in Table 3 can be used as cleaning compositions for cleaning surfaces or substrates.

TABLE 3

| Structure | Chemical Names |
|---|---|
| $CF_2=CHCF_2Br$ | 3-bromo-1,1,3,3-tetrafluoropropene |
| $CF_2=CFCBrH_2$ | 3-bromo-1,1,2-trifluoropropene |
| $CHF=CBrCF_3$ | 2-bromo-1,3,3,3-tetrafluoropropene |
| $CHF=CHCBrF_2$ | 3-bromo-1,3,3-trifluoropropene |
| $CHF=CBrCHF_2$ | 2-bromo-1,3,3-trifluoropropene |
| $CHBr=CFCF_3$ | 1-bromo-2,3,3,3-tetrafluoropropene |
| $CHBr=CHCF_3$ | 1-bromo-3,3,3-trifluoropropene |
| $CH_2=CBrCF_3$ | 2-bromo-3,3,3-trifluoropropene |
| $CH_2=CFCBrF_2$ | 3-bromo-2,3,3-trifluoropropene |
| $CFBr=CHCF_3$ | 1-bromo-1,3,3,3-tetrafluoropropene |
| $CFBr=CFCF_3$ | 1-bromopentafluoropropene |
| $CH_2=CBrCF_2CF_3$ | 2-bromo-3,3,4,4,4-pentafluoro-1-butene |
| $CHBr=CHCF_2CF_3$ | 1-bromo-3,3,4,4,4-pentafluoro-1-butene |
| $CH_2=CHCF_2CF_2Br$ | 4-bromo-3,3,4,4-tetrafluoro-1-butene |
| $CH_2=CHCBrFCF_3$ | 3-bromo-3,4,4,4-tetrafluoro-1-butene |
| $CF_3CBr=CFCF_3$ | 2-bromo-1,1,1,3,4,4,4-heptafluoro-2-butene |
| $CH_3CBr=CHCF_3$ | 2-bromo-4,4,4-trifluoro-2-butene |
| $CF_3CBr=CHCH_3$ | 2-bromo-1,1,1-trifluoro-2-butene |
| $(CF_3)_2C=CHBr$ | 1-bromo-3,3,3-trifluoro-2-(trifluoromethyl)-propene |
| $CF_3CF=CBrCF_2CF_3$ | 3-bromo-1,1,1,2,4,4,5,5,5-nonafluoro-2-pentene |
| $CHF_2CBr=CFC_2F_5$ | 2-bromo-1,1,3,4,4,5,5,5-octafluoro-2-pentene |
| $CF_2=CBrCHFC_2F_5$ | 2-bromo-1,1,3,4,4,5,5,5-octafluoro-1-pentene |
| $CHBr=CF(CF_2)_2CHF_2$ | 1-bromo-2,3,3,4,4,5,5-heptafluoro-1-pentene |
| $CH_2=CBrCF_2C_2F_5$ | 2-bromo-3,3,4,4,5,5,5-heptafluoro-1-pentene |
| $CF_2=CHCF_2CH_2CBrF_2$ | 5-bromo-1,1,3,3,5,5-hexafluoro-1-pentene |
| $(CF_3)_2CFCBr=CH_2$ | 2-bromo-3,4,4,4-tetrafluoro-3-(trifluoromethyl)-1-butene |
| $CF_2=C(CH_2Br)CF_3$ | 2-(bromomethyl)-1,1,3,3,3-pentafluoropropene |
| $CH_2=C(CBrF_2)CF_3$ | 2-(bromodifluoromethyl)-3,3,3-trifluoropropene |
| $(CF_3)_2CHCH=CHBr$ | 1-bromo-4,4,4-trifluoro-3-(trifluoromethyl)-1-butene |

TABLE 3-continued

| Structure | Chemical Names |
|---|---|
| $(CF_3)_2C=CHCH_2Br$ | 4-bromo-1,1,1-trifluoro-2-(trifluoromethyl)-2-butene |
| $CH_2=CHCF(CF_3)CBrF_2$ | 3-(bromodifluoromethyl)-3,4,4,4-tetrafluoro-1-butene |
| $CF_3CF_2CF_2CBr=CH_2$ | 2-bromo-3,3,4,4,5,5,5-heptafluoro-1-pentene |
| $CF_3(CF_2)_3CBr=CH_2$ | 2-bromo-3,3,4,4,5,5,6,6,6-nonafluoro-1-hexene |

The compounds listed in Table 3 are available commercially or may be prepared by processes known in the art.

1-Bromo-3,3,4,4,4-pentafluoro-1-butene may be prepared by a three-step sequence beginning with reaction of phosphorous tribromide with 3,3,4,4,4-pentafluoro-1-butanol to give 4-bromo-1,1,1,2,2-pentafluorobutane. Thermal bromination of 4-bromo-1,1,1,2,2-pentafluorobutane at 350-400° C. gives 4,4-dibromo-1,1,1,2,2-pentafluorobutane, which may in turn be heated with powdered potassium hydroxide to give the desired bromobutene.

2-Bromo-3,4,4,4-tetrafluoro-3-(trifluoromethyl)-1-butene may be prepared by addition of bromine to 3,4,4-tetrafluoro-3-(trifluoromethyl)-1-butene followed by treatment of the resulting dibromide with ethanolic potassium hydroxide.

In addition to the inventive compounds described above, the chlorine-containing unsaturated fluorinated hydrocarbons presented in Table 4 can be used as cleaning compositions for cleaning surfaces or substrates.

TABLE 4

| Structure | Chemical Names |
|---|---|
| $CHCl=CFCClF_2$ | 1,3-dichloro-2,3,3-trifluoro-1-propene |
| $CHCl=CClCF_3$ | 1,2-dichloro-3,3,3-trifluoro-1-propene |
| $CHCl=CHCH_2F$ | 1-chloro-3-fluoro-1-propene |
| $CHCl=CFCH_3$ | 1-chloro-2-fluoro-1-propene |
| $CH_2=CClCH_2F$ | 2-chloro-3-fluoro-1-propene |
| $CHF=CClCH_3$ | 2-chloro-1-fluoro-1-propene |
| $CH_2=CClCClF_2$ | 2,3-dichloro-3,3-difluoro-1-propene |
| $CH_2=CFCCl_2F$ | 3,3-dichloro-2,3-difluoro-1-propene |
| $CHCl=CClCHF_2$ | 1,2-dichloro-3,3-difluoro-1-propene |
| $CHCl=CHCClF_2$ | 1,3-dichloro-3,3-difluoro-1-propene |
| $CHF=CClCHClF$ | 2,3-dichloro-1,3-difluoro-1-propene |
| $CCl_2=CFCH_3$ | 1,1-dichloro-2-fluoro-1-propene |
| $CH_2=CClCHClF$ | 2,3-dichloro-3-fluoro-1-propene |
| $CH_2=C(CHF_2)CClF_2$ | 3-chloro-2-(difluoromethyl)-3,3-difluoro-1-propene |
| $CH_2=CHCF_2CHClF$ | 4-chloro-3,3,4-trifluoro-1-butene |
| $CHCl=C(CH_3)CF_3$ | 1-chloro-3,3,3-trifluoro-2-methyl-1-propene |
| $CH_2=CHCHClCF_3$ | 3-chloro-4,4,4-trifluoro-1-butene |
| $CH_3CF=CHCClF_2$ | 1-chloro-1,1,3-trifluoro-2-butene |
| $CH_2=CClCF_2CF_3$ | 2-chloro-3,3,4,4,4-pentafluoro-1-butene |
| $CHCl=CHCF_2CF_3$ | 1-chloro-3,3,4,4,4-pentafluoro-1-butene |
| $CH_2=CHCF_2CF_2Cl$ | 4-chloro-3,3,4,4-tetrafluoro-1-butene |
| $CH_2=CHCClFCF_3$ | 3-chloro-3,4,4,4-tetrafluoro-1-butene |
| $CH_3CCl=CHCF_3$ | 2-chloro-4,4,4-trifluoro-2-butene |
| $CF_3CCl=CHCH_3$ | 2-chloro-1,1,1-trifluoro-2-butene |
| $CH_2=CHCHClCHCl_2$ | 3,4,4-trichloro-3-fluoro-1-butene |
| $CH_2=CClCClFCClF_2$ | 2,3,4-trichloro-3,4,4-trifluoro-1-butene |
| $CH_2=CClCH_2CClF_2$ | 2,4-dichloro-4,4-difluoro-1-butene |
| $CH_2=CHCF_2CHCl_2$ | 4,4-dichloro-3,3-1-butene |

TABLE 4-continued

| Structure | Chemical Names |
|---|---|
| $CH_2$=CHCClFCClF$_2$ | 3,4-dichloro-3,4,4-trifluoro-1-butene |
| $CCl_2$=C(CH$_3$)CF$_3$ | 1,1-dichloro-3,3,3-trifluoro-2-methyl-1-propene |
| $CCl_2$=CHCH$_2$CF$_3$ | 1,1-dichloro-4,4,4-trifluoro-1-butene |
| $CH_2$=CFCClFCClF$_2$ | 3,4-dichloro-2,3,4,4-tetrafluoro-1-butene |
| CClF=CHC$_2$H$_5$ | 1-chloro-1-fluoro-1-butene |
| CHCl=CHCF$_2$CH$_3$ | 1-chloro-3,3-difluoro-1-butene |
| $CH_2$=CClCF$_2$CH$_3$ | 2-chloro-3,3-difluoro-1-butene |
| CH$_3$CH=CHCClF$_2$ | 4-chloro-4,4-difluoro-2-butene |
| (CF$_3$)$_2$C=CHCl | 1-chloro-3,3,3-trifluoro-2-(trifluoromethyl)-propene |
| CF$_3$CH=C(CClF$_2$)CF$_3$ | 2-(chlorodifluoromethyl)-1,1,1,4,4,4-hexafluoro-2-butene |
| CHCl=CHCF$_2$CClFCF$_3$ | 1,4-dichloro-3,3,4,5,5,5-hexafluoro-1-pentene |
| CHCl=CHCF(CClF$_2$)CF$_3$ | 1-chloro-3-(chlorodifluoromethyl)-3,4,4,4-tetrafluoro-1-butene |
| CF$_3$CF=CClCF$_2$CF$_3$ | 3-chloro-1,1,1,2,4,4,5,5,5-nonafluoro-2-pentene |
| CHCl=CF(CF$_2$)$_2$CHF$_2$ | 1-chloro-2,3,3,4,4,5,5-heptafluoro-1-pentene |
| $CH_2$=CClCF$_2$C$_2$F$_5$ | 2-chloro-3,3,4,4,5,5,5-heptafluoro-1-pentene |
| CF$_2$=CHCF$_2$CH$_2$CClF$_2$ | 5-chloro-1,1,3,3,5,5-hexafluoro-1-pentene |
| (CF$_3$)$_2$CFCCl=CH$_2$ | 2-chloro-3,4,4,4-tetrafluoro-3-(trifluoromethyl)-1-butene |
| (CF$_3$)$_2$CHCH=CHCl | 1-chloro-4,4,4-trifluoro-3-(trifluoromethyl)-1-butene |
| (CF$_3$)$_2$C=CHCH$_2$Cl | 4-chloro-1,1,1-trifluoro-2-(trifluoromethyl)-2-butene |
| $CH_2$=CHCF(CF$_3$)CClF$_2$ | 3-(chlorodifluoromethyl)-3,4,4,4-tetrafluoro-1-butene |
| $CH_2$=CClCF$_2$CF$_2$C$_2$F$_5$ | 2-chloro-3,3,4,4,5,5,6,6,6-nonafluoro-1-hexene |
| CHCl=CHCF$_2$CF$_2$C$_2$F$_5$ | 1-chloro-3,3,4,4,5,5,6,6,6-nonafluoro-1-hexene |

The compounds listed in Table 4 are available commercially or may be prepared by processes known in the art.

2-Chloro-3,3,4,4,4-pentafluoro-1-butene may be prepared by chlorination of 3,3,4,4,4-pentafluoro-1-butene to give 3,4-dichloro-1,1,1,2,2-pentafluoro-butane followed by reaction of the dichloride with ethanolic potassium hydroxide.

1-Chloro-3,3,4,4,4-pentafluoro-1-butene may be prepared by first photochlorinating 1,1,1,2,2-pentafluorobutane to give a mixture of terminally chlorinated pentafluorobutanes. After separating the 4,4-dichloro-1,1,1,2,2-pentafluorobutane by distillation, the dichloro derivative is refluxed with powdered potassium hydroxide to give the desired 1-chloro-3,3,4,4,4-pentafluoro-1-butene.

1-Chloro-2,3,3,4,4,5,5-heptafluoro-1-pentene may be prepared by reaction of 2,2,3,3,4,4,5,5-octafluoro-1-pentanol with dichlorotriphenylphosphorane followed by reaction of the resulting chloromethyl derivative with base as reported by Zapevalov, et. al. in the Russian Journal of Organic Chemistry, Vol. 24, pages 1466 to 1472 (1988).

2-Chloro-3,3,4,4,5,5,5-heptafluoro-1-pentene may be prepared by chlorination of 3,3,4,4,5,5,5-heptafluoro-1-pentene followed by treatment of the resulting dichloride with ethanolic potassium hydroxide.

2-Chloro-3,4,4,4-tetrafluoro-3-(trifluoromethyl)-1-butene may be prepared by chlorination of 3,4,4,4-tetrafluoro-3-(trifluoromethyl)-1-butene followed by treatment of the resulting dichloride with ethanolic potassium hydroxide.

2-Chloro-3,3,4,4,5,5,6,6,6-nonafluoro-1-hexene may be prepared by chlorination of 3,3,4,4,5,5,6,6,6-nonafluoro-1-hexene followed by treatment of the resulting dichloride with ethanolic potassium hydroxide.

1-Chloro-3,3,4,4,5,5,6,6,6-nonafluoro-1-hexene may be prepared by first photochlorinating 1,1,1,2,2,3,3,4,4-nonafluorohexane to give a mixture of terminally chlorinated pentafluorohexanes. After separating the 6,6-dichloro-1,1,1,2,2,3,3,4,4-nonafluorohexane by distillation, the dichloro derivative is refluxed with powdered potassium hydroxide to give the desired 1-chloro-3,3,4,4,5,5,6,6,6-nonafluoro-1-hexene. Cleaning compositions can comprise a single unsaturated fluorinated hydrocarbons as listed, for example, in Tables 3 or 4, or may comprise a combination of compounds from Table 3, a combination of compounds from Table 4, or, alternatively, a combination of compounds from any of Tables 2, 3 or 4 compounds and Formula I compounds. Such combinations of unsaturated fluorinated hydrocarbons may be utilized to optimize the solvency of a solvent composition for a particular solute.

Many of the compounds in Table 3 and Table 4 exist as different configurational isomers or stereoisomers. When the specific isomer is not designated, the present invention is intended to include all single configurational isomers, single stereoisomers, or any combination thereof. For instance, 2-bromo-1,3,3,3-tetrafluoropropene (CHF=CBrCF$_3$) is meant to represent the E-isomer, Z-isomer, or any combination or mixture of both isomers in any ratio. Another example is 1-chloro-1,3,3,3-tetrafluoropropene (CFCl=CHCF$_3$), by which is represented the E-isomer, Z-isomer, or any combination or mixture of both isomers in any ratio.

In one embodiment, the compositions disclosed have a Global Warming Potential (GWP) of not greater than 1000. In another embodiment, the compositions disclosed have a Global Warming Potential (GWP) of not greater than 500. In yet another embodiment, the compositions disclosed have a Global Warming Potential (GWP) of not greater than 150. In still yet another embodiment, the compositions disclosed have a Global Warming Potential (GWP) of not greater than 100. In still yet another embodiment, the compositions disclosed have a Global Warming Potential (GWP) of not greater than 50. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

In one embodiment, the present compositions have an Ozone Depletion Potential (ODP) of not greater than 0.05. In another embodiment, the present compositions have an Ozone Depletion Potential (ODP) of not greater than 0.02. In yet another embodiment, the present compositions have an Ozone Depletion Potential (ODP) of about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the unsaturated fluorinated hydrocarbons contained in the present compositions (e.g., from Formula I and Tables 2, 3, or 4) can vary widely, depending upon the particular application, and compositions containing more than trace amounts and less than 100% of the compound are within broad the scope of the present invention.

In one embodiment, the present compositions may further comprise an aerosol propellant. Aerosol propellant may assist in delivering the present composition from a storage container to a surface in the form of an aerosol. Aerosol propellant is optionally included in the present composition in up to about 25 weight percent of the total composition. Representative aerosol propellants comprise air, nitrogen, carbon dioxide, difluoromethane (CF$_2$H$_2$, HFC-32), trifluoromethane (CF$_3$H, HFC-23), difluoroethane (CHF$_2$CH$_3$, HFC-152a), trifluoroethane (CH$_3$CF$_3$, HFC-143a; or CHF$_2$CH$_2$F, HFC-143), tetrafluoroethane (CF$_3$CH$_2$F, HFC-134a; or CF$_2$HCF$_2$H, HFC-134), pentafluoroethane (CF$_3$CF$_2$H, HFC-125), and hydrocarbons, such as propane, butanes, or pentanes, or dimethyl ether.

In another embodiment, the present compositions may further comprise at least one surfactant. The surfactants of the present invention include all surfactants known in the art for dewatering or drying of substrates. Representative surfactants include alkyl phosphate amine salts (such as a 1:1 salt of 2-ethylhexyl amine and isooctyl phosphate); ethoxylated alcohols, mercaptans or alkylphenols; quaternary ammonium salts of alkyl phosphates (with fluoroalkyl groups on either the ammonium or phosphate groups); and mono- or di-alkyl phosphates of fluorinated amines. Additional fluorinated surfactant compounds are described in U.S. Pat. No. 5,908,822, incorporated herein by reference.

The amount of surfactant included in the dewatering compositions of the present invention can vary widely depending on the particular drying application in which said composition will be used, but is readily apparent to those skilled in the art. In one embodiment, the amount of surfactant dissolved in the unsaturated fluorinated hydrocarbon solvent is not greater than about 1 weight percent, based on the total weight of the surfactant/solvent composition. In another embodiment, larger amounts of surfactant can be used, if after treatment with the composition, the substrate being dried is thereafter treated with solvent containing either no or minimal surfactant. In one embodiment, the amount of surfactant is at least about 50 parts per million (ppm, on a weight basis). In another embodiment, the amount of surfactant is from about 100 to about 5000 ppm. In yet another embodiment, the amount of surfactant used is from about 200 to about 2000 ppm based on the total weight of the dewatering composition.

Optionally, other additives may be included in the present compositions comprising solvents and surfactants for use in dewatering. Such additives include compounds having anti-static properties; the ability to dissipate static charge from non-conductive substrates such as glass and silica. Use of an antistatic additive in the dewatering compositions of the present invention may be necessary to prevent spots and stains when drying water or aqueous solutions from electrically non-conductive parts such as glass lenses and mirrors. Most halocarbon solvents of the present invention also have utility as dielectric fluids, i.e., they are poor conductors of electric current and do not easily dissipate static charge. Boiling and general circulation of dewatering compositions in conventional drying and cleaning equipment can create static charge, particularly in the latter stages of the drying process where most of the water has been removed from a substrate. Such static charge collects on non-conductive surfaces of the substrate and prevents the release of water from the surface. The residual water dries in place resulting in undesirable spots and stains on the substrate. Static charge remaining on substrates can bring out impurities from the cleaning process or can attract impurities such as lint from the air, which results in unacceptable cleaning performance. In one embodiment, desirable antistatic additives are polar compounds, which are soluble in the present unsaturated fluorinated hydrocarbon solvent and result in an increase in the conductivity of the unsaturated fluorinated hydrocarbon solvent resulting in dissipation of static charge from a substrate. In another embodiment, the antistatic additives have a normal boiling point near that of the unsaturated fluorinated hydrocarbon solvent and have minimal to no solubility in water. In yet another embodiment, the antistatic additives have a solubility in water of less than about 0.5 weight percent. In one embodiment, the solubility of antistatic agent is at least 0.5 weight percent in unsaturated fluorinated hydrocarbon solvent. In one embodiment, the antistatic additive is nitromethane ($CH_3NO_2$).

In one embodiment, the present dewatering composition containing an antistatic additive is effective in both the dewatering and drying and rinse steps of a method to dewater or dry a substrate as described below.

Another embodiment relates to a method for dewatering or drying a substrate comprising:
 a) contacting the substrate with a composition of the present invention containing surfactant, thereby dewatering said substrate and
 b) recovering the dewatered substrate from the composition.

Many industries use aqueous compositions for the surface treatment of metals, ceramics, glasses, and plastics. Cleaning, plating, and deposition of coatings are often carried out in aqueous media and are usually followed by a step in which residual water is removed. Hot air drying, centrifugal drying, and solvent-based water displacement are methods used to remove such residual water.

While hydrofluorocarbons (HFCs) have been proposed as replacements for the previously used CFC solvents in drying or dewatering applications, many HFCs have limited solvency for water. The use of surfactant, which assists in removal of water from substrates is therefore necessary in many drying or dewatering methods. Hydrophobic surfactants have been added to dewatering or drying solvents to displace water from substrates.

The primary function of the dewatering or drying solvent (unsaturated fluorinated hydrocarbon solvent) in a dewatering or drying composition is to reduce the amount of water on the surface of a substrate being dried. The primary function of the surfactant is to displace any remaining water from the surface of the substrate. When the unsaturated fluorinated hydrocarbon solvent and surfactant are combined, a highly effective displacement drying composition is attained.

In one embodiment, drying or dewatering solvents of the disclosure include those unsaturated fluorinated hydrocarbon compounds listed in Table 1 and Table 2.

In one embodiment the fluorinated olefins for dewatering or drying of a substrate from Table 1 and Table 2 have normal boiling points of from about 25° C. to about 120° C.

In one embodiment, the surfactant for dewatering and drying is soluble to at least 1 weight percent based on the total solvent/surfactant composition weight.

In one embodiment, the dewatering or drying method of the present disclosure is very effective in displacing water from a broad range of substrates including metals, such as tungsten, copper, gold, beryllium, stainless steel, aluminum alloys, brass and the like; from glasses and ceramic surfaces, such as glass, sapphire, borosilicate glass, alumina, silica such as silicon wafers used in electronic circuits, fired alumina and the like; and from plastics such as polyolefin ("Alathon", Rynite®, "Tenite"), polyvinylchloride, polystyrene (Styron), polytetrafluoroethylene (Teflon®), tetrafluoroethylene-ethylene copolymers (Tefzel®), polyvinylidenefluoride ("Kynar"), ionomers (Surlyn®), acrylonitrile-butadiene-styrene polymers (Kralac®), phenol-formaldehyde copolymers, cellulosic ("Ethocel"), epoxy resins, polyacetal (Delrin®), poly (p-phenylene oxide) (Noryl®), polyetherketone ("Ultrapek"), polyetheretherketone ("Victrex"), poly(butylene terephthalate) ("Valox"), polyarylate (Arylon®), liquid crystal polymer, polyimide (Vespel®), polyetherimides ("Ultem"), polyamideimides ("Torlon"), poly(p-phenylene sulfide) ("Rython"), polysulfone ("Udel"), and polyaryl sulfone ("Rydel"). In another embodiment, the compositions for use in the present dewatering or drying method are compatible with elastomers.

In one embodiment, the disclosure is directed to a process for removing at least a portion of water from, i.e., dewatering, the surface of a wetted substrate, which comprises contacting the substrate with the aforementioned dewatering composition, and then removing the substrate from contact with the dewatering composition. In one embodiment, water originally bound to the surface of the substrate is displaced by solvent and/or surfactant and leaves with the dewatering composition. By "at least a portion of water" is meant at least about 75 weight percent of water at the surface of a substrate is removed per immersion cycle. By "immersion cycle" is meant one cycle involving at least a step wherein substrate is immersed in the present dewatering composition. Optionally, minimal amounts of surfactant remaining adhered to the substrate can be further removed by contacting the substrate with surfactant-free halocarbon solvent. Holding the article in the solvent vapor or refluxing solvent will further decrease the presence of surfactant remaining on the substrate. Removal of solvent adhering to the surface of the substrate is effected by evaporation. Evaporation of solvent at atmospheric or subatmospheric pressures can be employed and temperatures above and below the boiling point of the halocarbon solvent can be used.

Methods of contacting the substrate with dewatering composition are not critical and can vary widely. For example, the substrate can be immersed in the composition, or the substrate can be sprayed with the composition using conventional equipment. Complete immersion of the substrate is preferred as it generally insures contact between the composition and all exposed surfaces of the substrate. However, any other method, which can easily provide such complete contact may be used.

The time period over which substrate and dewatering composition are contacted can vary widely. Usually, the contacting time is up to about 5 minutes, however, longer times may be used if desired. In one embodiment of the dewatering process, the contacting time is from about 1 second to about 5 minutes. In another embodiment, the contacting time of the dewatering process is from about 15 seconds to about 4 minutes.

Contacting temperatures can also vary widely depending on the boiling point of the composition. In general, the contacting temperature is equal to or less than the composition's normal boiling point.

In one embodiment, the compositions of the present disclosure may further contain a co-solvent. Such co-solvents are desirable where the present compositions are employed in cleaning conventional process residue from substrates, e.g., removing soldering fluxes and degreasing mechanical components comprising substrates of the present invention. Such co-solvents include alcohols (such as methanol, ethanol, isopropanol), ethers (such as diethyl ether, methyl tertiary-butyl ether), ketones (such as acetone), esters (such as ethyl acetate, methyl dodecanoate, isopropyl myristate and the dimethyl or diisobutyl esters of succinic, glutaric or adipic acids or mixtures thereof), ether alcohols (such as propylene glycol monopropyl ether, dipropylene glycol monobutyl ether, and tripropylene glycol monomethyl ether), and hydrocarbons (such as pentane, cyclopentane, hexane, cyclohexane, heptane, octane), and hydrochlorocarbons (such as trans-1,2-dichloroethylene). When such a co-solvent is employed with the present composition for substrate dewatering or cleaning, it may be present in an amount of from about 1 weight percent to about 50 weight percent based on the weight of the overall composition.

In cleaning apparatuses, including vapor degreasing and vapor defluxing equipment, compositions may be lost during operation through leaks in shaft seals, hose connections, soldered joints and broken lines. In addition, the working composition may be released to the atmosphere during maintenance procedures on equipment. If the composition is not a pure component, the composition may change when leaked or discharged to the atmosphere from the equipment, which may cause the composition remaining in the equipment to exhibit unacceptable performance. Accordingly, it is desirable to use as a cleaning composition comprising a single unsaturated fluorinated hydrocarbon.

In one embodiment, the compositions of the present disclosure are useful as cleaning compositions, cleaning agents, deposition solvents and as dewatering or drying solvents. For proper operation in use, microelectronic components must be cleaned of flux residues, oils and greases, and particulates that may contaminate the surfaces after completion of manufacture. In another embodiment, the present disclosure relates to a process for removing residue from a surface or substrate comprising contacting the surface or substrate with a cleaning composition or cleaning agent of the present invention and, optionally, recovering the surface or substrate substantially free of residue from the cleaning composition or cleaning agent.

In yet another embodiment, the present disclosure relates to a method for cleaning surfaces by removing contaminants from the surface. The method for removing contaminants from a surface comprises contacting the surface having contaminants with a cleaning composition of the present invention to solubilize the contaminants and, optionally, recovering the surface from the cleaning composition. The surface is then substantially free of contaminants.

As stated previously, the contaminants or residues that may be removed by the present method include, but are not limited to oils and greases, flux residues, and particulate contaminants.

In one embodiment of the method, the contacting may be accomplished by spraying, flushing, wiping with a substrate e.g., wiping cloth or paper, that has the cleaning composition incorporated in or on it. In another embodiment of the method, the contacting may be accomplished by dipping or immersing the disk in a bath of the cleaning composition.

In one embodiment of the method, the recovering is by removing the surface that has been contacted from the cleaning composition bath (in a similar manner as described for the method for depositing an a fluorolubricant on a surface as described below). In another embodiment of the method, the recovering is by allowing the cleaning composition that has been sprayed, flushed, or wiped on the disk to drain away. Additionally, any residual cleaning composition that may be left behind after the completion of the previous steps may be evaporated in a manner similar to that for the deposition method as well.

The method for cleaning a surface may be applied to the same types of surfaces as the method for deposition as described below. Semiconductor surfaces or magnetic media disks of silica, glass, metal or metal oxide, or carbon may have contaminants removed by the method. In the method described above, contaminant may be removed from a disk by contacting the disk with the cleaning composition and recovering the disk from the cleaning composition.

In yet another embodiment, the present method also provides methods of removing contaminants from a product, part, component, substrate, or any other article or portion thereof by contacting the article with a cleaning composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material. Hydrocarbon based oils and greases and dioctylphthalate are examples of the contaminants that may be found on the carbon coated disks.

In one embodiment, the present method comprises contacting the article with a cleaning composition of the invention, in a vapor degreasing and solvent cleaning method. In one such embodiment, vapor degreasing and solvent cleaning methods consist of exposing an article, preferably at room temperature, to the vapors of a boiling cleaning composition. Vapors condensing on the object have the advantage of providing a relatively clean, distilled cleaning composition to wash away grease or other contamination. Such processes thus have an additional advantage in that final evaporation of the present cleaning composition from the object leaves behind relatively little residue as compared to the case where the object is simply washed in liquid cleaning composition.

In another embodiment, for applications in which the article includes contaminants that are difficult to remove, the present methods involve raising the temperature of the cleaning composition above ambient or to any other temperature that is effective in such application to substantially improve the cleaning action of the cleaning composition. In one such embodiment, such processes are also generally used for large volume assembly line operations where the cleaning of the article, particularly metal parts and assemblies, must be done efficiently and quickly.

In one embodiment, the cleaning methods of the present invention comprise immersing the article to be cleaned in liquid cleaning composition at an elevated temperature. In another embodiment, the cleaning methods of the present invention comprise immersing the article to be cleaned in liquid cleaning composition at about the boiling point of the cleaning composition. In one such embodiment, this step removes a substantial amount of the target contaminant from the article. In yet another embodiment, this step removes a major portion of the target contaminant from the article. In one embodiment, this step is then followed by immersing the article in freshly distilled cleaning composition, which is at a temperature below the temperature of the liquid cleaning composition in the preceding immersion step. In one such embodiment, the freshly distilled cleaning composition is at about ambient or room temperature In yet another embodiment, the method also includes the step of then contacting the article with relatively hot vapor of the cleaning composition, by exposing the article to vapors rising from the hot/boiling cleaning composition associated with the first mentioned immersion step. In one such embodiment, this results in condensation of the cleaning composition vapor on the article. In certain preferred embodiments, the article may be sprayed with distilled cleaning composition before final rinsing.

It is contemplated that numerous varieties and types of vapor degreasing equipment are adaptable for use in connection with the present methods. One example of such equipment and its operation is disclosed by U.S. Pat. No. 3,085,918, which is incorporated herein by reference. The equipment disclosed therein includes a boiling sump for containing a cleaning composition, a clean sump for containing distilled cleaning composition, a water separator, and other ancillary equipment.

The present cleaning methods may also comprise cold cleaning in which the contaminated article is either immersed in the fluid cleaning composition of the present invention under ambient or room temperature conditions or wiped under such conditions with rags or similar objects soaked in the cleaning composition.

The present invention also relates to a method for depositing a fluorolubricant of the invention on a surface, said method comprising combining the fluorolubricant with a solvent comprising an unsaturated fluorinated hydrocarbon of the present invention, contacting said combination of fluorolubricant and solvent with the surface and evaporating the solvent to form a fluorolubricant coating on the surface.

The most advanced, highest recording densities and lowest cost method of storing digital information involves writing and reading magnetic flux patterns from rotating disks coated with magnetic materials. A magnetic layer, where information is stored in the form of bits, is sputtered onto a metallic support structure. Next an overcoat, usually a carbon-based material, is placed on top of the magnetic layer for protection and finally a lubricant is applied to the overcoat. A read-write head flies above the lubricant and the information is exchanged between the head and the magnetic layer. In a relentless attempt to increase the efficiency of information transfer, hard drive manufacturers have reduced the distance between the head and the magnetic layer, or fly-height, to less than 100 Angstroms.

Invariably, during normal disk drive application, the head and the disk surface will make contact. To reduce wear on the disk, from both sliding and flying contacts, it must be lubricated.

Fluorolubricants are widely used as lubricants in the magnetic disk drive industry to decrease the friction between the head and disk, that is, reduce the wear and therefore minimize the possibility of disk failure.

There is a need in the industry for improved methods for deposition of fluorolubricants. The use of certain solvents, such as CFC-113 and PFC-5060, has been regulated due to their impact on the environment. Therefore, solvents that will be used in this application should consider environmental impact. Also, such solvent must dissolve the fluorolubricant and form a substantially uniform or uniform coating of fluorolubricant. Additionally, existing solvents have been found to require higher fluorolubricant concentrations to produce a given thickness coating and produce irregularities in uniformity of the fluorolubricant coating.

In one embodiment, the fluorolubricants of the present disclosure comprise perfluoropolyether (PFPE) compounds, or lubricant comprising X-1P®, which is a phosphazene-containing disk lubricant. These perfluoropolyether compounds are sometimes referred to as perfluoroalkylethers (PFAE) or perfluoropolyalkylethers (PFPAE). These PFPE compounds range from simple perfluorinated ether polymers to functionalized perfluorinated ether polymers. PFPE compounds of different varieties that may be useful as fluorolubricant in the present invention are available from several sources. In another embodiment, useful fluorolubricants for the present inventive method include but are not limited to Krytox® GLP 100, GLP 105 or GLP 160 (E.I. du Pont de Nemours & Co., Fluoroproducts, Wilmington, Del., 19898, USA); Fomblin® Z-Dol 2000, 2500 or 4000, Z-Tetraol, or Fomblin® AM 2001 or AM 3001 (sold by Solvay Solexis S.p.A., Milan, Italy); Demnum™ LR-200 or S-65 (offered by Daikin America, Inc., Osaka, Japan); X-1P® (a partially fluorinated hyxaphenoxy cyclotriphosphazene disk lubricant available from Quixtor Technologies Corporation, a subsidiary of Dow Chemical Co, Midland, Mich.); and mixtures thereof. The Krytox® lubricants are perfluoroalkylpolyethers having the general structure $F(CF(CF_3)CF_2O)_n$—$CF_2CF_3$, wherein n ranges from 10 to 60. The Fomblin® lubricants are functionalized perfluoropolyethers that range in molecular weight from 500 to 4000 atomic mass units and have general formula $X-CF_2-O(CF_2-CF_2-O)_p-(CF_2O)_q-CF_2-X$, wherein X may be $-CH_2OH$, $CH_2(O-CH_2-CH_2)_nOH$, $CH_2OCH_2CH(OH)CH_2OH$ or $-CH_2O-CH_2$-piperonyl. The Demnum™ oils are perfluoropolyether-based oils ranging in molecular weight from 2700 to 8400 atomic mass units. Additionally, new lubricants are being developed such as those from Moresco (Thailand) Co., Ltd, which may be useful in the present inventive method.

The fluorolubricants of the present invention may additionally comprise additives to improve the properties of the fluorolubricant. X-1P®, which may serve as the lubricant itself, is often added to other lower cost fluorolubricants in order to increase the durability of disk drives by passivating Lewis acid sites on the disk surface responsible for PFPE degradation.

Other common lubricant additives may be used in the fluorolubricants of the present inventive methods.

The fluorolubricants of the present invention may further comprise Z-DPA (Hitachi Global Storage Technologies, San Jose, Calif.), a PFPE terminated with dialkylamine end-groups. The nucleophilic end-groups serve the same purpose as X1P®, thus providing the same stability without any additive.

The surface on which the fluorolubricant may be deposited is any solid surface that may benefit from lubrication. Semiconductor materials such as silica disks, metal or metal oxide surfaces, vapor deposited carbon surfaces or glass surfaces are representative of the types of surfaces for which the methods of the present invention are useful. The present inventive method is particularly useful in coating magnetic media such as computer drive hard disks. In the manufacture of computer disks, the surface may be a glass, or aluminum substrate with layers of magnetic media that is also coated by vapor deposition with a thin (10-50 Angstrom) layer of amorphous hydrogenated or nitrogenated carbon. The fluorolubricant may be deposited on the surface disk indirectly by applying the fluorolubricant to the carbon layer of the disk.

The first step of combining the fluorolubricant and solvent may be accomplished in any suitable manner such as mixing in a suitable container such as a beaker or other container that may be used as a bath for the deposition method. The fluorolubricant concentration in the unsaturated fluorinated hydrocarbon solvent may be from about 0.010 percent (wt/wt) to about 0.50 percent (wt/wt).

The step of contacting said combination of fluorolubricant and solvent with the surface may be accomplished in any manner appropriate for said surface (considering the size and shape of the surface). A hard drive disk must be supported in some manner such as with a mandrel or some other support that may fit through the hole in the center of the disk. The disk will thus be held vertically such that the plane of the disk is perpendicular to the solvent bath. The mandrel may have different shapes including but not limited to, a cylindrical bar, or a V-shaped bar. The mandrel shape will determine the area of contact with the disk. The mandrel may be constructed of any material strong enough to hold the disk, including but not limited to metal, metal alloy, plastic or glass. Additionally, a disk may be supported vertically upright in a woven basket or be clamped into a vertical position with 1 or more clamps on the outer edge. The support may be constructed of any material with the strength to hold the disk, such as metal, metal alloy, plastic or glass. However the disk is supported, the disk will be lowered into a container holding a bath of the fluorolubricant/solvent combination. The bath may be held at room temperature or be heated or cooled to temperatures ranging from about 0° C. to about 50° C.

Alternatively, the disk may be supported as described above and the bath may be raised to immerse the disk. In either case, the disk may then be removed from the bath (either by lowering the bath or by raising the disk). Excess fluorolubricant/solvent combination can be drained into the bath.

Either of the methods for contacting the fluorolubricant/solvent combination with the disk surface of either lowering the disk into a bath or raising a bath to immerse the disk are commonly referred to as dip coating. Other methods for contacting the disk with the fluorolubricant/solvent combination may be used in the present inventive method, including spraying or spin coating.

When the disk is removed from the bath, the disk will have a coating of fluorolubricant and some residual solvent (unsaturated fluorinated hydrocarbon) on its surface. The residual solvent may be evaporated. Evaporation is usually performed at room temperature. However, other temperatures both above and below room temperature may be used as well for the evaporation step. Temperatures ranging from about 0° C. to about 100° C. may be used for evaporation.

The surface, or the disk if the surface is a disk, after completion of the coating method, will be left with a substantially uniform or uniform coating of fluorolubricant that is substantially free of solvent. The fluorolubricant may be applied to a thickness of less than about 300 nm, and alternately to a thickness of about 100 to about 300 nm.

A uniform fluorolubricant coating is desired for proper functioning of a disk and so areas of varying fluorolubricant thickness are undesirable on the surface of the disk. As more and more information is being stored on the same size disk, the read/write head must get closer and closer to the disk in order to function properly. If irregularities due to variation in coating thickness are present on the surface of the disk, the probability of contact of the head with these areas on the disk is much greater. While there is a desire to have enough fluorolubricant on the disk to flow into areas where it may be removed by head contact or other means, coating that is too thick may cause "smear," a problem associated with the read/write head picking up excess fluorolubricant.

One specific coating thickness irregularity observed in the industry is that known as the "rabbit ears" effect. These irregularities are visually detected on the surface of the disk after deposition of the fluorolubricant using the existing solvent systems. When the disk is contacted with the solution of fluorolubricant in solvent and then removed from the solution, any points where the solution may accumulate and not drain readily develop drops of solution that do not readily drain off. One such point of drop formation is the contact point (or points) with the mandrel or other support device with the disk. When a V-shaped mandrel is used, there are two contact points at which the mandrel contacts the inside edge of the disk. When solution of fluorolubricant forms drops in these locations that do not drain off when removed from the bath, an area of greater thickness of fluorolubricant is created when the solvent evaporates. The two points of contact with the disk produces what is known as a "rabbit ears" effect, because the areas of greater fluorolubricant thickness produce a pattern resembling rabbit ears visually detectable on the disk surface.

When dip coating is used for depositing fluorolubricant on the surface, the pulling-up speed (speed at which the disk is removed from the bath), and the density of the fluorolubricant and the surface tension are relevant for determining the resulting film thickness of the fluorolubricant. Awareness of these parameters for obtaining the desired film thickness is required. Details on how these parameters effect coatings are given in, "Dip-Coating of Ultra-Thin Liquid Lubricant and its Control for Thin-Film Magnetic Hard Disks" in IEEE Transactions on Magnetics, vol. 31, no. 6, November 1995.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain cleaning compositions or cleaning agents which are chemically related may be substituted for the compositions described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modifications of the invention to adapt it to various uses and conditions.

Example 1

Synthesis of 1,1,1,4,4,5,5,6,6,7,7,7-dodecafluorohept-2-ene (F14E)

Synthesis of $C_4F_9CH_2CHICF_3$

Perfluoro-n-butyliodide (180.1 gm, 0.52 moles) and 2,2,2-trifluoropropene (25.0 gm, 0.26 moles) were added to a 400 ml Hastelloy™ shaker tube and heated to 200° C. for 8 hours under autogenous pressure, which increased to a maximum of 428 psig (3.05 Mpa). The product was collected at room temperature. The above reaction was carried out again at these conditions and the products combined. It was then repeated doubling the amount of perfluoro-n-butyliodide and 2,2,2-trifluoropropene in the same 400 ml reactor. In this case the pressure increased to 573 psig (3.85 Mpa). The products of the three reactions were combined and distilled to give 322.4 gm of $C_4F_9CH_2CHICF_3$ (52.2°/35 mm) in 70% yield.
Conversion of $C_4F_9CH_2CHICF_3$ to F14E $C_4F_9CH_2CHICF_3$ (322.4 gm, 0.73 moles) was added dropwise via addition funnel to a 2 L round bottom flask equipped with stir a bar and connected to a packed distillation column and still head. The flask contained isopropyl alcohol (95 ml), KOH (303.7 gm, 0.54 moles) and water (303 ml). Product was collected, washed with sodium metabisulfite, water, dried with $MgSO_4$ and distilled through a 6" column filled with glass helices. The product, F14E (173.4 gm, 76%) boils at 78.2° C. It was characterized by $^{19}F$ NMR ($\delta$ −66.7 ($CF_3$, m, 3F), −81.7 ($CF_3$, m 3F), −124.8 ($CF_2$, m, 2F), −126.4 ($CF_2$, m, 2F), and −114.9 ppm ($CF_2$, m, 2F)) $^1H$ NMR ($\delta$ 6.45) in chloroform-d solution.

Example 2

Synthesis of 1,1,1,2,2,5,5,6,6,7,7,8,8,8-tetradecafluorooct-3-ene (F24E)

Synthesis of $C_4F_9CHICH_2C_2F_5$

Perfluoroethyliodide (220 gm, 0.895 mole) and 3,3,4,4,5,5,6,6,6-nonafluorohex-1-ene (123 gm, 0.50 mole) were added to a 400 ml Hastelloy™ shaker tube and heated to 200° C. for 10 hours under autogenous pressure. The product from this and two others carried out under similar conditions were combined and washed with two 200 mL portions of 10 wt % aqueous sodium bisulfite. The organic phase was dried over calcium chloride and then distilled to give 277.4 gm of $C_4F_9CH_2CHICF_3$ (79-81° C./67-68 mm Hg) in 37% yield.
Conversion of $C_4F_9CHICH_2C_2F_5$ to F24E A 1 L round bottom flask equipped with a mechanical stirrer, addition funnel, condenser, and thermocouple was charged with $C_4F_9CHICH_2C_2F_5$ (277.4 gm, 0.56 moles) and isopropanol (217.8 g). The addition funnel was charged with a solution of potassium hydroxide (74.5 g, 1.13 moles) dissolved in 83.8 g of water. The KOH solution was added dropwise to the flask with rapid stirring over the course of about one hour as the temperature slowly increased from 21° C. to 42° C. The reaction mass was diluted with water and the product recovered by phase separation. The product was washed with 50 mL portions of 10 wt % aqueous sodium bisulfite and water, dried over calcium chloride, and then distilled at atmospheric pressure. The product, F24E (128.7 gm, 63%) boils at 95.5° C. It was characterized by $^{19}F$ NMR ($\delta$ −81.6 ($CF_3$, m, 3F), −85.4 ($CF_3$, m 3F), −114.7 ($CF_2$, m, 2F), −118.1 ($CF_2$, m, 2F), −124.8 ppm ($CF_2$, m, 2F), −126.3 ppm ($CF_2$, m, 2F)) and $^1H$ NMR ($\delta$ 6.48) in chloroform-d solution.

Example 3

Synthesis of $CF_3CH=CHCF(CF_3)_2$(F13iE)

Synthesis of $CF_3CHICH_2CF(CF_3)_2$ $(CF_3)_2CFI$ (265 gm, 0.9 mole) and 2,2,2-trifluoropropene (44.0 gm, 0.45 mole) were added to a 400 ml Hastelloy™ shaker tube and heated to 200° C. for 8 hours under autogenous pressure (maximum of 585 psig (4.14 MPa)). The product was collected at room temperature to give 110 gm of $(CF_3)_2CFCH_2CHICF_3$ (76-77° C./200 mm) in 62% yield.
Conversion of $(CF_3)_2CFCH_2CHICF_3$ to F13iE A 500 ml round bottom flask was equipped with stir a bar and an addition funnel and connected to a short path distillation column and dry ice trap. The flask was charged with isopropyl alcohol (50 ml), potassium hydroxide (109 gm, 1.96 moles), and water (109 ml). $(CF_3)_2CFCH_2CHICF_3$ (109 gm, 0.28 mole) was slowly added dropwise via the addition funnel at 42° C. During the addition, the temperature increased from 42 to 55° C. and the product distilled out of the flask. After refluxing for 30 minutes, the temperature in the flask increased to 62° C. Product was collected, washed with water, dried with $MgSO_4$ and distilled. The product, F13iE (41 gm, 55%), boils at 48-50° C. and was characterized by 19F NMR ($\delta$ −187.6 (CF, m 1F), −77.1 (CF3, m 6F), −66.3 (CF3, m 3F) in chloroform-d solution.

Example 4

Synthesis of C4F9CHICH2C2F5

3,3,4,4,5,5,6,6,6-Nonafluorohex-1-ene (20.5 gm, 0.0833 mole), bis(triphenyl phosphine)nickel(0) dicarbonyl (0.53 g, 0.0008 mole), and perfluoroethyliodide (153.6 gm, 0.625 mole) were added to a 210 ml Hastelloy™ shaker tube and heated at 100° C. for 8 hours under autogenous pressure. Analysis of the product by GC-MS indicated the presence of C4F9CHICH2CH2F5 (64.3 GC area %) and the diadduct (3.3 GC area %); the conversion of 3,3,4,4,5,5,6,6,6-nonafluoro-hex-1-ene was 80.1%.

Example 5

The ability of unsaturated fluoroolefin compounds to dissolve a fluorinated oil was determined by adding an amount of the oil to the unsaturated fluoroolefin compound until the mixture became turbid or separated into two phases. The results in Table 1 show that the unsaturated fluoroolefin compound has high ability to dissolve the fluorinated oil. In addition, a solution of 0.5 wt % of the oil was prepared in the unsaturated fluoroolefin compound. In this example, the unsaturated fluoroolefin was 1,1,1,2,2,5,5,6,6,7,7,8,8,8-tetradecafluorooct-3-ene (F24E). Preweighed metal coupons were dipped into the solution, the solvent evaporated, and the coupon re-weighed. Table 5 shows the average coating obtained by this dip coating process. Thus, unsaturated fluoroolefin compounds can be used as carrier fluids for the deposition of the fluorinated oil onto a substrate.

TABLE 5

| Oil | Solubility in F24E | Coating thickness |
|---|---|---|
| Krytox GPL 102 oil | miscible | 2.9 μg/cm$^2$ |
| Krytox GPL 106 oil | miscible | 22.9 μg/cm$^2$ |

Example 6

Krytox GPL 106 Oil was wiped onto a clean metal coupon, of known weight, with a swab. The coupon was weighed again and then cleaned by immersion into 1,1,1,2,2,5,5,6,6,7,7,8,8,8-tetradecafluorooct-3-ene (F24E) at the room temperature. The coupon was immersed for 1 minute then air dried. The coupon was then reweighed and the percent of oil removed was determined. These results in Table 6 show that the solvent has excellent efficiency in cleaning fluorinated oils.

TABLE 6

| Sample | Wt. of coupon before coating | Wt of coupon after coating with Krytox oil | Wt of coupon after cleaning | Percent soil removed |
|---|---|---|---|---|
| 1 | 10.6782 | 10.7384 | 10.6786 | 99 |
| 2 | 10.4968 | 10.5328 | 10.4967 | 100 |
| 3 | 10.7183 | 10.7498 | 10.7183 | 100 |

We claim:

1. The solvent composition consisting essentially of $CF_3CH=CHCF(CF_3)_2$.

2. The composition of claim 1 further consisting essentially of a propellant.

3. The composition of claim 2 wherein the propellant is selected from the group consisting of air, nitrogen, carbon dioxide, difluoromethane ($CF_2H_2$, HFC-32), trifluoromethane ($CF_3H$, HFC-23), difluoroethane ($CHF_2CH_3$, HFC-152a), trifluoroethane ($CH_3CF_3$, HFC-143a; or $CHF_2CH_2F$, HFC-143), tetrafluoroethane ($CF_3CH_2F$, HFC-134a; or $CF_2HCF_2H$, HFC-134), pentafluoroethane ($CF_3CF_2H$, HFC-125), and hydrocarbons, such as propane, butanes, or pentanes, or dimethyl ether.

4. The composition of claim 1 further consisting essentially of a surfactant.

5. A method for removing residue from a surface comprising:
   a. contacting the surface with a composition comprising an unsaturated fluorinated hydrocarbon having the formula E- or Z—$R^1CH=CHR^2$, wherein $R^1$ is $CF_3$ and $R^2$ is $CF(CF_3)_2$, and
   b. recovering the surface from the composition.

6. The method of claim 5 wherein said composition further comprises an aerosol propellant.

7. The method of claim 5 wherein said composition further comprises a surfactant.

8. The method of claim 5 wherein said composition further comprises a co-solvent.

9. The method of claim 5 wherein the contacting is accomplished by vapor degreasing.

10. The method of claim 9, wherein the vapor degreasing is performed by:
    (i) boiling the composition; and
    (ii) exposing the article to vapors of the boiling cleaning composition.

11. The method of claim 5, wherein the contacting is accomplished by immersing the article in said composition, wherein the composition is at a temperature greater than ambient or room temperature.

12. The method of claim 11, wherein the composition is at a temperature of about the boiling point of the composition.

13. The method of claim 5, wherein the contacting is accomplished by wiping the article with an object soaked in the composition.

14. A method for depositing a fluorolubricant on a surface comprising:
    (a) combining a fluorolubricant and a solvent, said solvent comprising an unsaturated fluorinated hydrocarbon having the formula E- or Z—$R^1CH=CHR^2$, wherein $R^1$ is $CF_3$ and $R^2$ is $CF(CF_3)_2$ to form a lubricant-solvent combination;
    (b) contacting the combination of lubricant-solvent with the surface; and
    (c) evaporating the solvent from the surface to form a fluorolubricant coating on the surface.

15. The method of claim 14, wherein the surface is that of a semiconductor material, metal, metal oxide, vapor deposited carbon, or glass.

16. The method of claim 14, wherein the surface is that of a magnetic medium.

17. The method of claim 16, wherein the magnetic medium is a computer disk.

18. The method of claim 14, wherein the contacting step is accomplished by dipping or immersing the surface in a bath comprising the fluorolubricant.

19. The method of claim 14, wherein the contacting step is accomplished by spraying or spin coating the surface with the fluorolubricant.

20. The method of claim 14, wherein the fluorolubricant concentration in the lubricant-solvent combination is from about 0.02 weight percent to about 0.5 weight percent.

21. The method of claim 14, wherein the evaporating step is accomplished at a temperature of from about 10° C. to about 40° C.

22. The method of claim 14, wherein the fluorolubricant comprises a perfluoropolyether.

23. The method of claim 14, wherein the fluorolubricant is selected from the group consisting of perfluoropolyethers and mixtures thereof.

24. A process for removing at least a portion of water from the surface of a wetted substrate, said process comprising:
 a) contacting the substrate with the composition of claim 1, wherein the composition further consists essentially of a surfactant, and then
 b) removing the substrate from contact with said composition.

* * * * *